United States Patent
Donners et al.

(10) Patent No.: US 11,118,025 B2
(45) Date of Patent: Sep. 14, 2021

(54) LYOPHILIZED FOAMS OF END BLOCK-CONTAINING ABSORBABLE POLYMERS

(71) Applicant: Ethicon, Inc., Somerville, NJ (US)

(72) Inventors: Jackie Donners, Pennington, NJ (US); Marc Wisnudel, Millburn, NJ (US); Mark Timmer, Jersey City, NJ (US)

(73) Assignee: Ethicon, Inc., Somerville, NJ (US)

( * ) Notice: Subject to any disclaimer, the term of this patent is extended or adjusted under 35 U.S.C. 154(b) by 680 days.

(21) Appl. No.: 15/864,207

(22) Filed: Jan. 8, 2018

(65) Prior Publication Data

US 2018/0127560 A1 May 10, 2018

Related U.S. Application Data

(62) Division of application No. 14/728,226, filed on Jun. 2, 2015, now Pat. No. 9,896,560.

(51) Int. Cl.
| | |
|---|---|
| *C08J 9/26* | (2006.01) |
| *C08G 63/08* | (2006.01) |
| *A61L 27/18* | (2006.01) |
| *A61L 27/56* | (2006.01) |
| *A61L 27/58* | (2006.01) |
| *A61L 31/06* | (2006.01) |

(Continued)

(52) U.S. Cl.
CPC ............... *C08J 9/26* (2013.01); *A61L 27/18* (2013.01); *A61L 27/56* (2013.01); *A61L 27/58* (2013.01); *A61L 31/06* (2013.01); *A61L 31/146* (2013.01); *A61L 31/148* (2013.01); *C08G 63/08* (2013.01); *C08J 9/36* (2013.01); *C08J 2201/048* (2013.01); *C08J 2201/0482* (2013.01); *C08J 2205/02* (2013.01); *C08J 2205/05* (2013.01); *C08J 2207/10* (2013.01); *C08J 2300/16* (2013.01); *C08J 2367/04* (2013.01)

(58) Field of Classification Search
CPC ................... C08J 2201/048; C08J 2201/0482
See application file for complete search history.

(56) References Cited

U.S. PATENT DOCUMENTS

| | | | |
|---|---|---|---|
| 4,605,730 | A | 8/1986 | Shalaby et al. |
| 4,700,704 | A | 10/1987 | Jamiolkowski et al. |
| 4,788,979 | A | 12/1988 | Jarrett et al. |

(Continued)

FOREIGN PATENT DOCUMENTS

| | | |
|---|---|---|
| CN | 1159456 A | 9/1997 |
| CN | 1211582 A | 3/1999 |

(Continued)

OTHER PUBLICATIONS

Karimi, M. et al. "Formation and Size Distribution of Pores in Poly (ε-caprolactone) Foams Prepared by Pressure Quenching Using Supercritical $CO_2$", Journal of Supercritical Fluids, 61, (2012) pp. 175-190.

(Continued)

*Primary Examiner* — Alison L Hindenlang
*Assistant Examiner* — George W. Brady
(74) *Attorney, Agent, or Firm* — David R. Crichton

(57) ABSTRACT

Novel absorbable foams, lyophilizing solutions, and lyophilizing and annealing processes are disclosed. The foams are made from copolymers of glycolide and epsilon-caprolactone. The foams are useful in or as implantable medical devices.

9 Claims, 7 Drawing Sheets

Schematic representation of the polymer

(51) Int. Cl.
*A61L 31/14* (2006.01)
*C08J 9/36* (2006.01)

(56) References Cited

U.S. PATENT DOCUMENTS

| | | | |
|---|---|---|---|
| 5,102,983 | A | 4/1992 | Kennedy |
| 5,133,739 | A | 7/1992 | Bezwada et al. |
| 5,431,679 | A | 7/1995 | Bennett et al. |
| 5,468,253 | A | 11/1995 | Bezwada et al. |
| 5,633,343 | A | 5/1997 | Bezwada et al. |
| 5,713,920 | A | 2/1998 | Bezwada et al. |
| 5,854,383 | A | 12/1998 | Erneta et al. |
| 6,306,424 | B1 | 10/2001 | Vyakarnam et al. |
| 6,325,810 | B1 | 12/2001 | Hamilton et al. |
| 6,333,029 | B1 | 12/2001 | Vyakarnam et al. |
| 6,355,699 | B1 | 3/2002 | Vyakarnam et al. |
| 6,712,850 | B2 | 3/2004 | Vyakarnam et al. |
| 6,770,717 | B2 | 8/2004 | Kim et al. |
| 6,946,143 | B2 | 9/2005 | Kim et al. |
| 7,148,315 | B2 | 12/2006 | Erneta et al. |
| 7,435,789 | B2 | 10/2008 | Shalaby |
| 8,278,409 | B2 | 10/2012 | Erneta et al. |
| 8,481,651 | B2 | 7/2013 | Hissink et al. |
| 8,674,032 | B2 | 3/2014 | Hissink et al. |
| 2003/0105525 | A1 | 6/2003 | Vyakamam et al. |
| 2003/0193104 | A1 | 10/2003 | Melican et al. |
| 2007/0154512 | A1* | 7/2007 | Dave .................. A61F 2/82 424/423 |
| 2009/0004271 | A1 | 1/2009 | Brown et al. |
| 2014/0072609 | A1 | 3/2014 | Pacetti et al. |
| 2016/0354510 | A1 | 12/2016 | Andjelic et al. |

FOREIGN PATENT DOCUMENTS

| | | |
|---|---|---|
| CN | 102369026 A | 3/2012 |
| CN | 104640903 A | 5/2015 |
| JP | 63-145661 A | 6/1988 |
| JP | 1-284262 | 11/1989 |
| JP | 4-213320 A | 4/1992 |
| JP | 6-277274 | 10/1994 |
| JP | 9-12689 A | 1/1997 |
| JP | 11-181077 A | 7/1999 |
| JP | 2001-49018 A | 2/2001 |
| JP | 2002-291867 A | 10/2002 |
| JP | 2012-522871 A | 9/2012 |
| WO | 2008/016667 A2 | 2/2008 |
| WO | 2014149801 A1 | 9/2014 |

OTHER PUBLICATIONS

Schugens, C. et al. "Polylactide Macroporous Biodegradable Implants for Cell Transplantation. II. Preparation of Polylactide Foams by Liquid-Liquid Phase Separation", Journal of Biomedical Materials Research, vol. 30, (1996) pp. 449-461.

Barry, J.J. et al. "Supercritical Carbon Dioxide: Putting the Fizz into Biomaterials", Phil. Trans. R. Soc. A, (2006) vol. 364, pp. 249-261.

Min, et al., Biodegradable Shape-Memory Polymer-Polyactide-Co-Poly(Glycolide-co-caprolactone) multiblock copolymer. Polymers for Advanced Technologies, 2005, pp. 608-615, vol. 16, No. 8.

\* cited by examiner

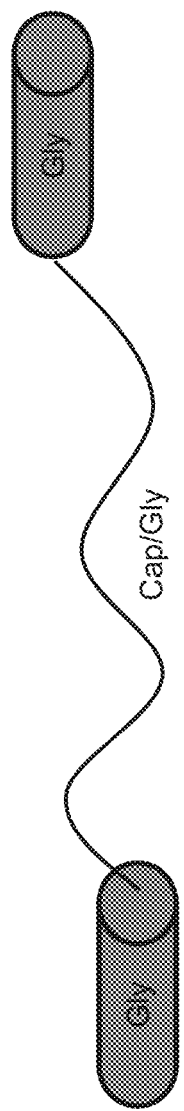
Figure 1: Schematic representation of the polymer

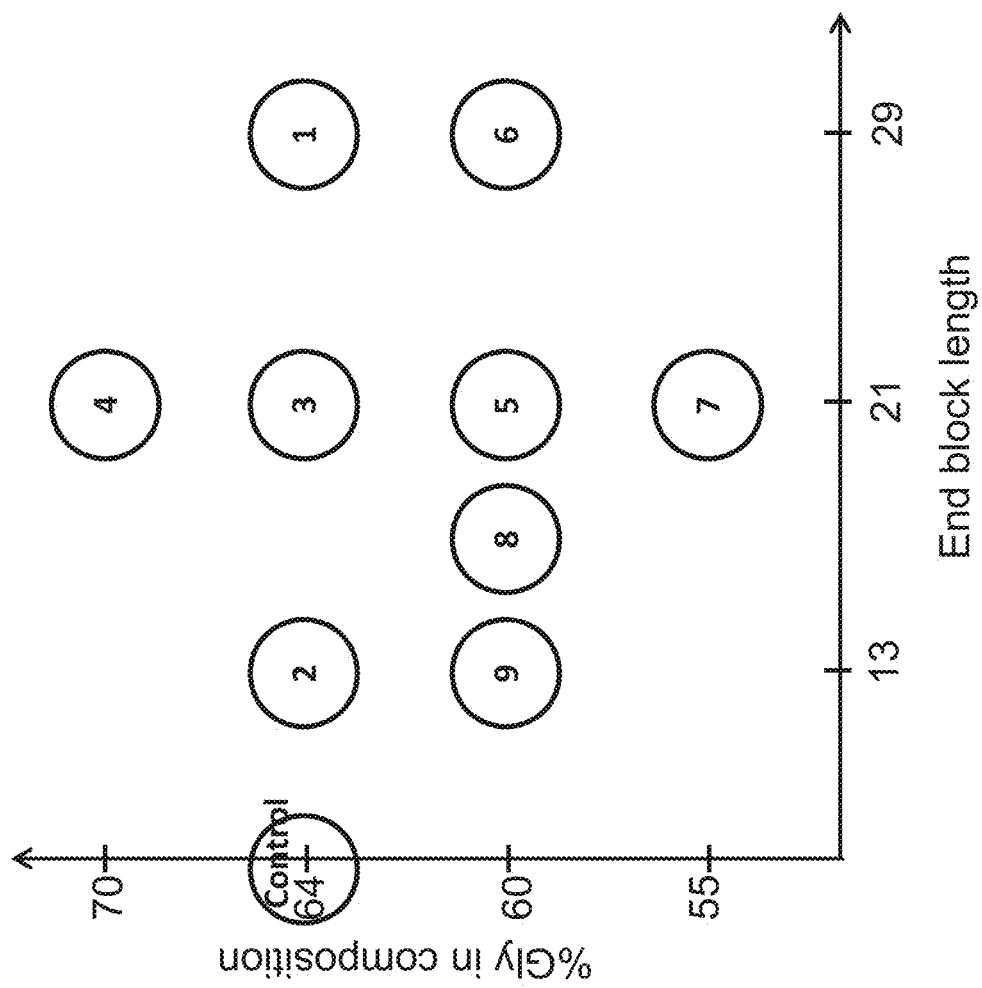
Figure 2: Graphical representation of the compositions of the polymers of the present invention

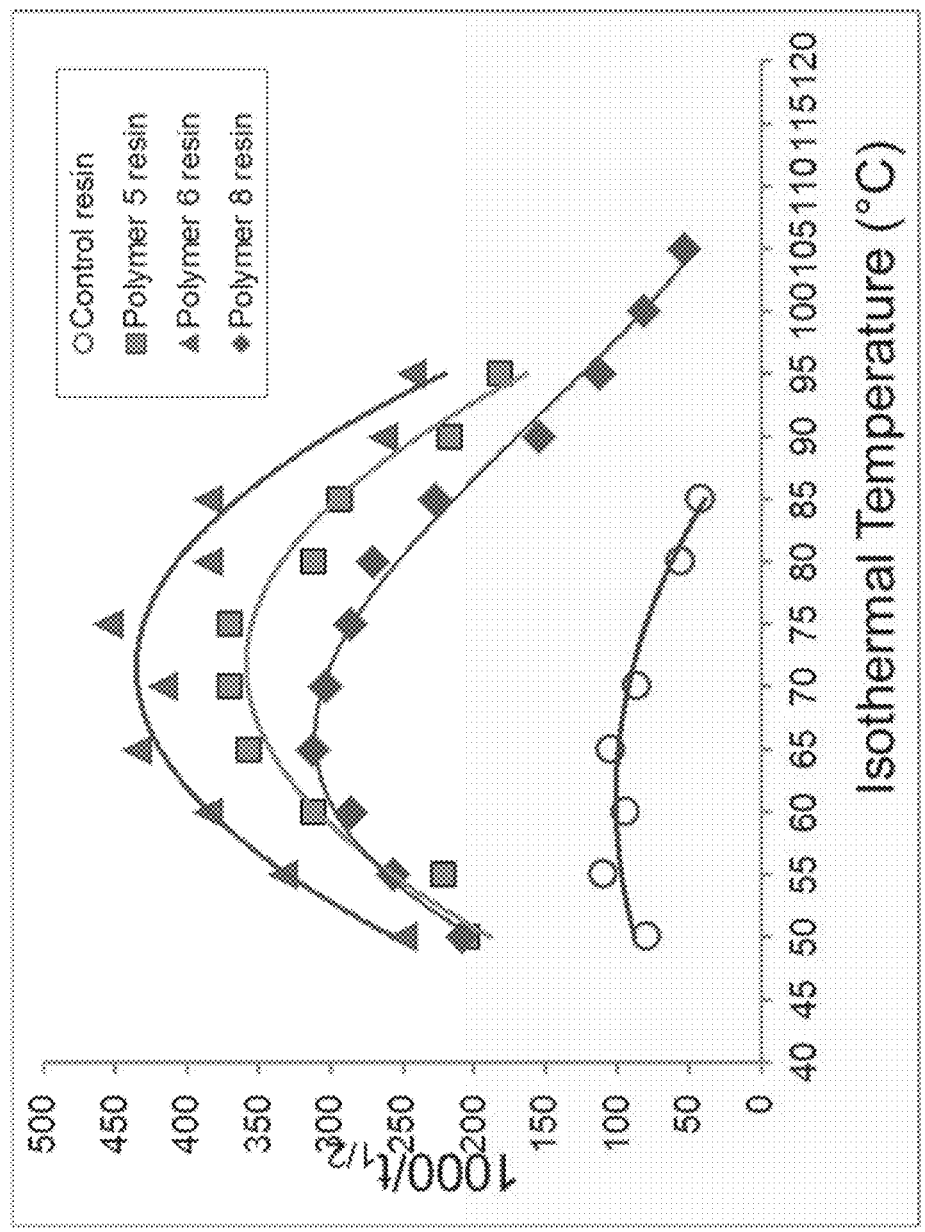
Figure 3: Isothermal crystallization curves for selected lots

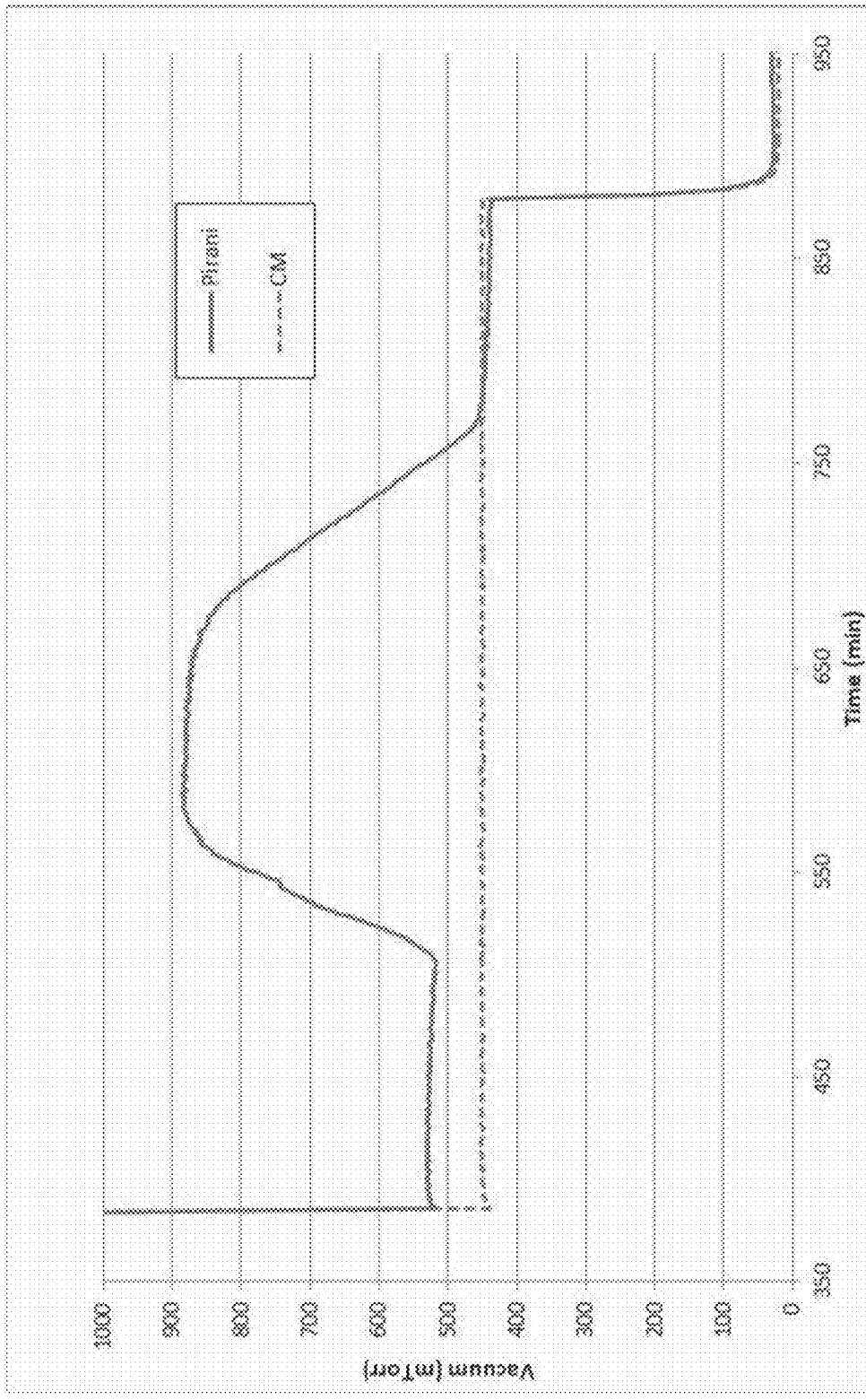

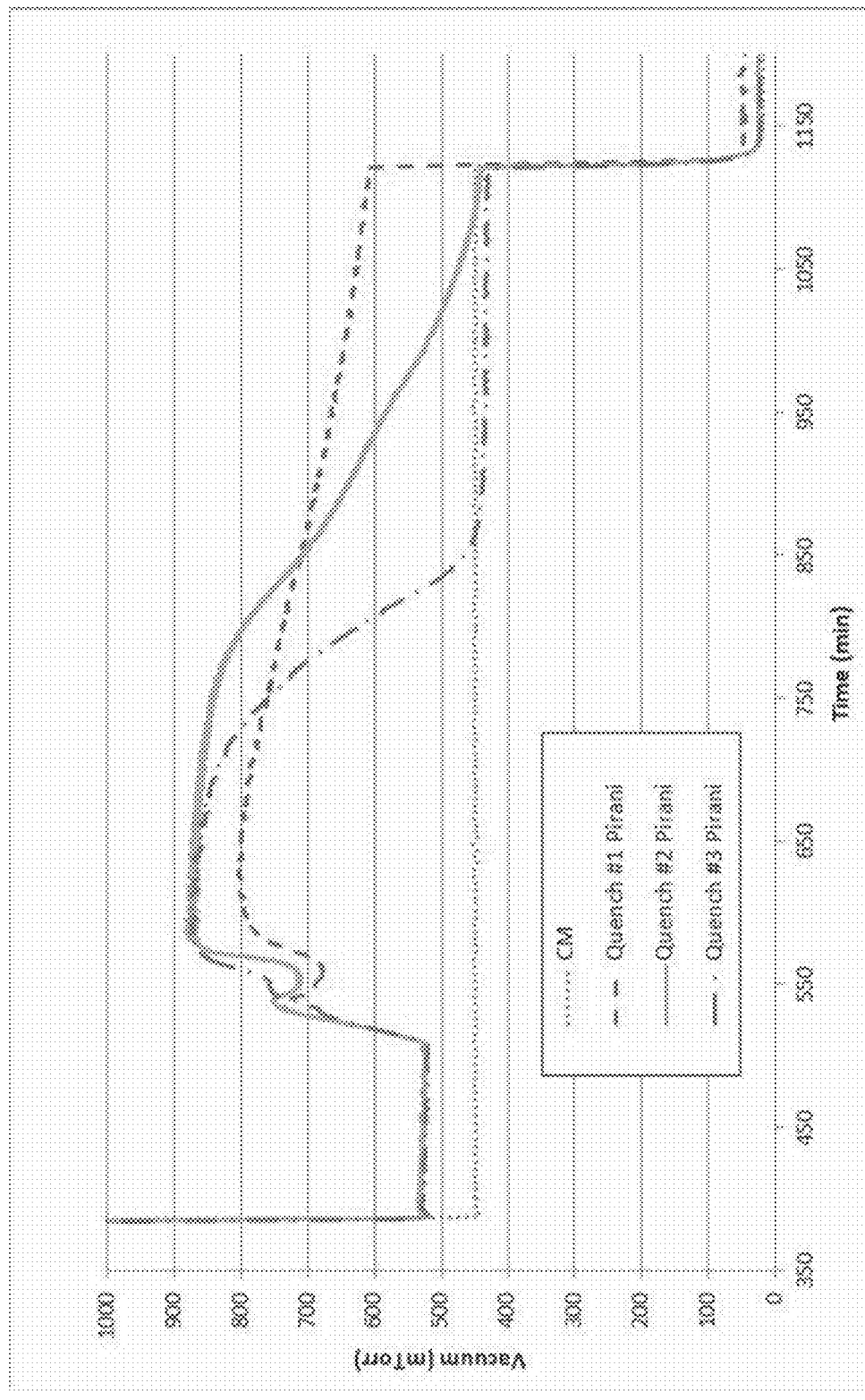
Figure 5: Primary drying profile for lyophilization of inventive segmented block copolymer solutions with different quench methods

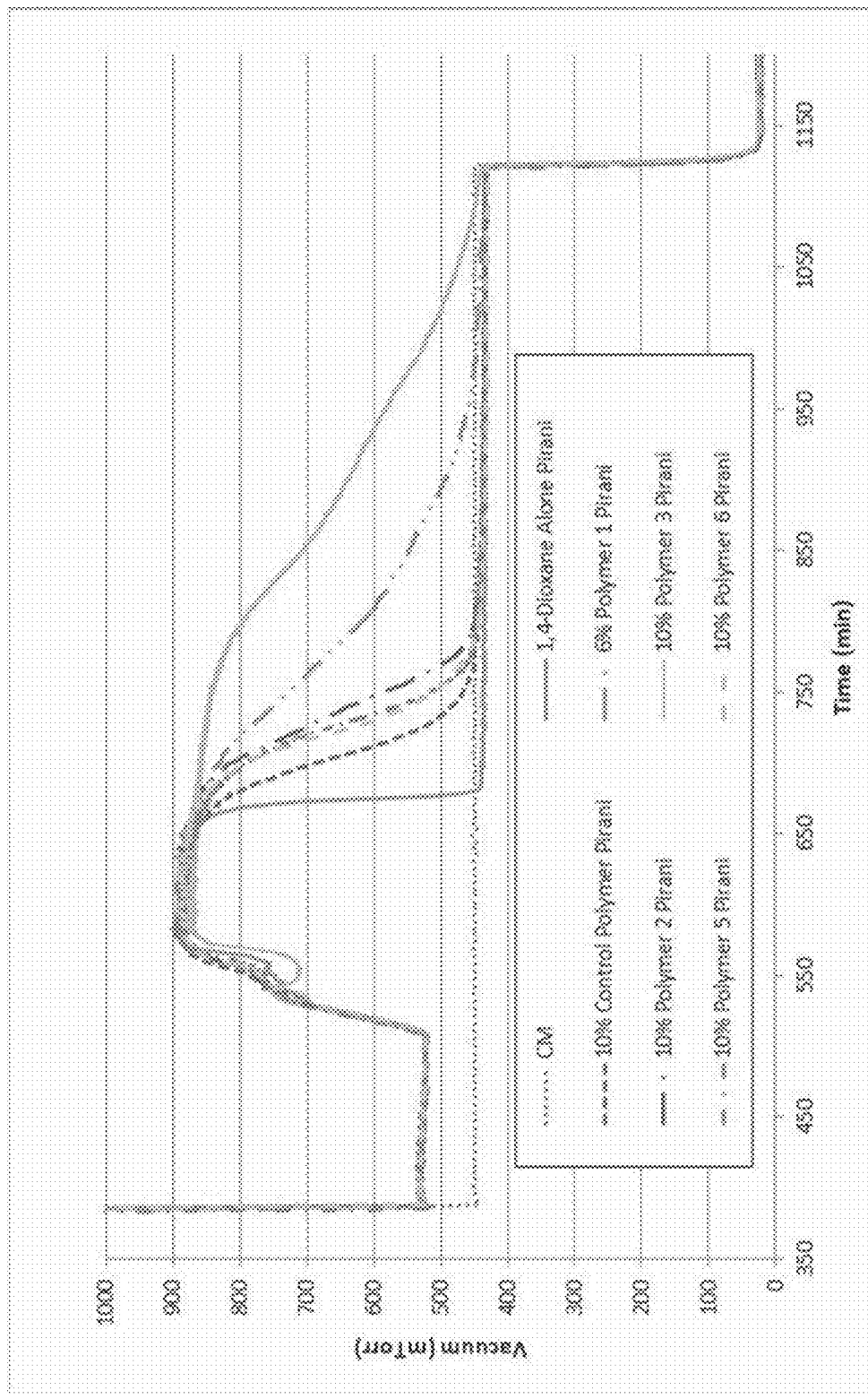
Figure 6: Primary drying profile for lyophilization of inventive segmented block copolymer solutions with different gelation times

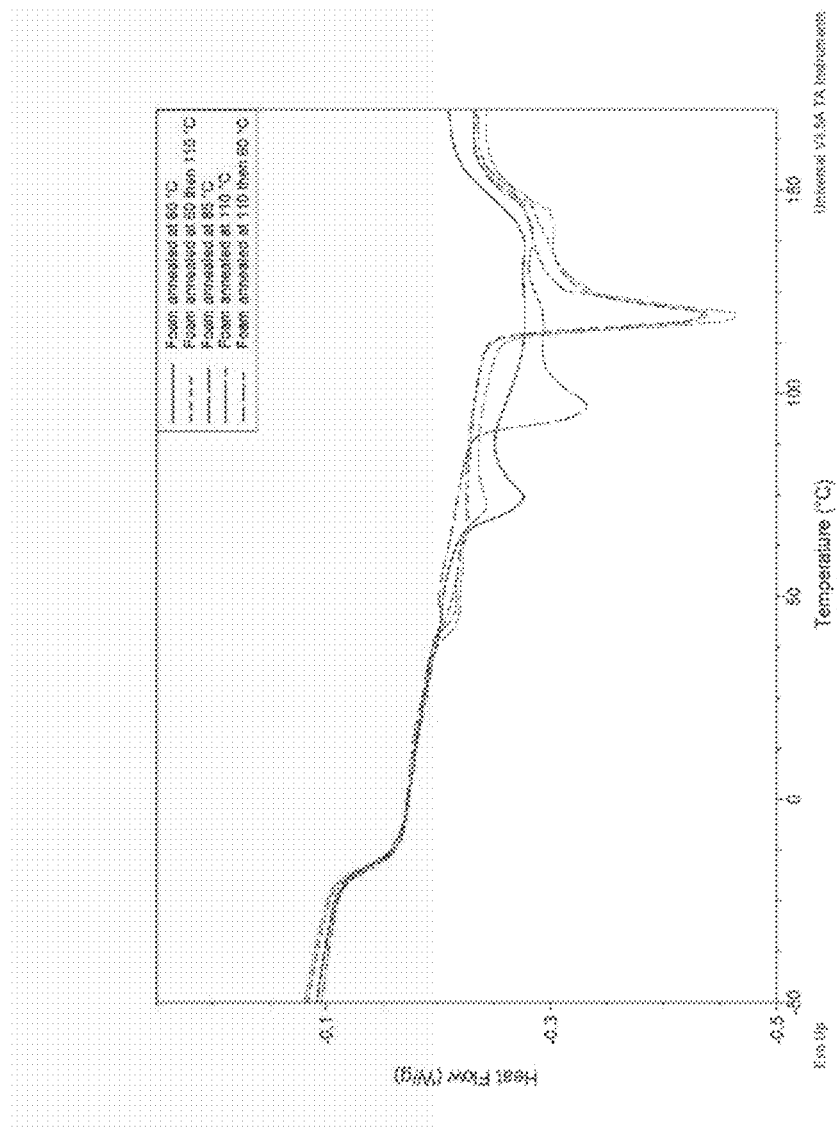
Figure 7: DSC thermograms of foams based on polymer 5 annealed at various temperatures

LYOPHILIZED FOAMS OF END BLOCK-CONTAINING ABSORBABLE POLYMERS

FIELD OF THE INVENTION

This invention relates to novel absorbable polymers, more particularly semi-crystalline block copolymers of ε-caprolactone and glycolide that are suitable for absorbable medical devices in particular lyophilized foams.

BACKGROUND OF THE INVENTION

Synthetic absorbable polyester polymers are well known in the art. The open, scientific, and patent literature particularly describe polymers and copolymers made from glycolide, L(−)-lactide, D(+)-lactide, meso-lactide, epsilon-caprolactone, p-dioxanone, and trimethylene carbonate. Such polymers are conventionally used to manufacture absorbable medical devices.

A very important aspect of any absorbable medical device is the length of time that its mechanical properties are retained in vivo. For example, in many surgical applications it is important for the device to retain strength for a sufficient length of time to allow the body the time necessary to heal while effectively performing its desired function.

Medical devices in the form of polymeric foams are known in the art. What does not presently exist is an absorbable polymer that can be made into a foam that is soft enough to exhibit mechanical elasticity to provide spring-back after being compressed and superior handling characteristics to the surgeon, yet maintain its mechanical properties post-implantation to function effectively long term, while fully absorbing. There then remains the problem of providing such a polymer that can meet these needs. There is also a need for an absorbable surgical foam made from such a polymer.

Absorbable foams generally come in two basic forms, open cell structures and closed cell structures. Open cell foams are particularly advantageous for tissue engineering applications requiring cell ingrowth. Buttress designs of various types made from, biocompatible polymers have been described for use with mechanical surgical staplers. One function of a buttress is to reinforce a surgical staple line. However, an implantable absorbable foam having a utility as a buttress has yet to be provided that meets long term needs.

Foam formation from polymeric materials has been described by various researchers over the years. For instance, foams have been made by melt processes such as extrusion with blowing agents and utilizing supercritical carbon dioxide.

For example, the use of supercritical carbon dioxide in making foams is disclosed in "Formation and Size distribution of Pores in Poly(ε-Caprolactone) Foams Prepared by Pressure Quenching using Supercritical $CO_2$", by Karimi, et. al., *J. of Supercritical Fluids,* 61 (2012) 175-190. The use of supercritical carbon dioxide in making foams is also disclosed in "Supercritical Carbon Dioxide: Putting the Fizz into Biomaterials", Barry, et. al, *Phil. Trans. R. Soc. A,* 2006 364, 249-261.

Lyophilization processes are well known in the art and have been used to prepare open cell foams from synthetic absorbable materials. These processes are not without difficulties, however. The polymer to be lyophilized must be soluble in the selected solvent, and there are only a limited number of solvents that are suitable for a lyophilization process. The freezing point of a successful solvent needs to be above that of a reasonable shelf and condenser temperature (~−70° C.), and low enough to conveniently dissolve the resin to be lyophilized. Moreover, the vapor pressure at low temperature needs to be high enough so that the solvent can be sublimated from the frozen state at a reasonable enough rate. Typical solvents conventionally used in lyophilization processes include water, 1,4-dioxane, DMSO, DMF, and certain alcohols. Most absorbable polyesters are hydrophobic in nature while the solvents suitable for lyophilization tend to be polar in nature; accordingly, this creates solubility issues since it is the rare absorbable polymer that can be dissolved in an appropriate lyophilizing solvent.

The final architecture of a polymeric foam made by lyophilization depends on a number of factors, including the polymer concentration in the solvent. Higher mechanical properties often correlate with the bulk density of the foam. High densities then require higher concentrations of the dissolved polymer; for example, 10 weight percent initial solids dissolved in the lyophilizing solvent versus 3 weight percent initial solids. Although a given polymer may be considered soluble in a solvent, it may not be soluble at the high concentrations that may be needed in foam medical devices. Even those absorbable polymers that are soluble in solvents suitable for lyophilization may present another difficulty arising from the phenomena of premature gel formation. Premature gel formation is known to interfere with the making of homogeneous foams, as is required. Premature gelation is particularly challenging in high concentration solutions. It is believed that the gelation phenomena may be due to inter- and intra-chain molecular associations, similar to what might occur during crystallization in solids, although not as strongly. Once gelation takes place in a lyophilizing polymer solution, it is very difficult for polymer chains to possess the mobility that they need during the phase separation which must occur as the pure solvent (i.e., solvent without dissolved polymer) crystallizes. Individual chains are "fixed" in place and cannot disentangle to join a solvent/polymer phase of ever increasing polymer concentration.

With regard to the typical lyophilization process from a manufacturing standpoint, it would be desirable that polymer solutions take longer than 180 minutes to form gels. This would provide sufficient time to dispense the solution into molds, load said molds into the lyophilization unit or other thermal treatment system, and freeze before the formation of the undesirable gels.

It has been noted that solutions having higher polymer concentrations may be achieved by lowering the molecular weight of the given polymer. However, this has the disadvantage of lowering the mechanical properties of the resultant foam to unacceptable levels for most surgical applications.

Absorbable polymeric foams used in medical applications must typically exhibit dimensional stability, that is, the foams must not deform while undergoing additional post-processing treatments such as ethylene oxide sterilization, transportation, warehouse storage, and such. This is often a challenge when working with polymers possessing low glass transition temperatures since molecular mobility is enhanced, thereby readily allowing warping, shrinking and other distortions. The crystallization of the polymer constituting the foam is one means of achieving dimensional stability. It should be noted however that a polymer having too high a level of crystallinity in the foam may result in a final article which is too stiff for a given surgical application.

For example, the level of "spring back" may be inadequate. Thus, important mechanical properties may be influenced not only by the polymer itself ($T_g$, etc.) but also by the polymer morphology that develops in the final product, again greatly influenced by the polymer and its thermal history. The level of crystallinity in the resin prior to attempted dissolution in a lyophilizing solvent is also important in low $T_g$ resins. If the crystallinity is too low the resin pellet (or ground resin) may begin to stick to itself during storage or transportation if exposed to even the slightest elevated temperatures, for example 20° C. The once divided, free-flowing polymer granules gradually aggregate into a large brick-like mass. If the crystallinity of the resin is too high, difficulties may be experienced during attempts to dissolve the resin in the selected solvent; that is, the resin may not properly dissolve.

The lyophilization process is known to be demanding in that it is difficult to produce a suitable product in a robust fashion. If the polymer does not readily dissolve, if it tends to form gels too quickly, if it cannot maintain dimensional stability during the process (as, well as later during EU sterilization or during transportation), or if the solvent cannot be adequately removed, a suitable foam will not result.

Of course being able to make an absorbable polymeric foam with an appropriate architecture does not complete the challenge; it is necessary to provide a foam with appropriate ester chemistry to achieve an appropriate hydrolysis profile post-implantation. Retention of mechanical properties for a number of long term surgical applications is critical in slow to heal patients or in slow to heal bodily tissue. Finally, the polymer must still be absorbable; that is, slowly hydrolyze in vivo so that it can be removed by the body from the surgical site.

The polymer must, then, possess certain solubility and crystallization characteristics, as well as certain mechanical and hydrolysis properties, if it is to be suitable for fabricating surgical foam products by the lyophilization method.

The use of some absorbable synthetic polyesters for foam formation via lyophilization processes is known and disclosed in the art. Examples include, U.S. Pat. No. 5,468,253, Bezwada, et al., "Elastomeric Medical Device", filed on Jan. 21, 1993 and issued on Nov. 21, 1995, which discloses medical devices or components for medical devices formed from by bioabsorbable elastomers comprising a random copolymer of from about 30 to about 70 weight percent of: a) ε-caprolactone, trimethylene carbonate, and ether lactone, or a mixture of these, and b) the balance being substantially glycolide, para-dioxanone, or a mixture thereof. U.S. Pat. No. 5,468,253 further discloses bioabsorbable foams made from the elastomers.

U.S. Pat. No. 6,355,699, Vyakarnam, et al., "Process for Manufacturing Biomedical Foams" filed on Jun. 30, 1999 and issued on Mar. 12, 2002 discloses an improved lyophilization process for forming biocompatible foam structures.

The ε-caprolactone/glycolide copolyesters described by Vyakarnam et al. are directed toward elastomeric materials (see col 5, lines 32 to 36). Their one-step, one-pot polymerization process method tends to produce polymers that exhibit a random distribution of monomer repeat units. In general, the substantially random copolymers of Bezwada, et al and Vyakarnam et al. are quite soluble in at least one lyophilization solvent, 1,4-dioxane, and only form the undesired gels after an extended period of time. This last characteristic is valuable from a manufacturing standpoint in that it allows significant leeway in processing times. An undesirable characteristic, however, of the random s-caprolactone/glycolide copolyesters described by Bezwada et al. is that their copolymers are able achieve only low levels of crystallinity. This is a very important characteristic because these copolymers possess relatively low glass transition temperatures and thus do not have the required crystallinity to achieve dimensional stability.

Accordingly, there is a need in the art for novel absorbable polymeric foams to be used in medical applications. Specifically in the case of absorbable foams, there is a need to provide retention of mechanical properties post-implantation for extended periods of time. Additionally, there is need to provide foams with improved dimensional stability to avoid warping, shrinking and other distortions during sterilization, storage, transportation, or an exposure to slightly elevated temperatures. Furthermore, there is a need to provide absorbable foams possessing appropriate stiffness, being neither too soft nor too hard, that allow good "springback" upon compression; this requires a proper range of crystallinity and $T_g$.

Finally, there exists a need to provide an absorbable polymer possessing an adequate crystallization rate and the ability to achieve an adequate crystallization level so as to be able to form dimensionally stable foams by a lyophilization process.

SUMMARY OF THE INVENTION

Novel foams made from semi-crystalline, block copolymers of glycolide and epsilon-caprolactone for absorbable medical applications are disclosed. The semicrystalline absorbable segmented copolymers have a random segment of repeating units of polymerized glycolide and polymerized epsilon-caprolactone and at least one segment that comprises predominantly polymerized glycolide. The mole ratio of polymerized glycolide to polymerized epsilon-caprolactone of the entire segmented copolymer is between about 55:45 to about 65:35. The mole ratio of polymerized glycolide to polymerized epsilon-caprolactone in the random segment between about 45:55 to about 60:40.

In a preferred embodiment, the novel foams of the present invention possess a solids content between about 3 weight percent and about 20 weight percent, more preferably about 5 weight percent and about 15 weight percent. The foams of the present invention preferably have a thickness between about 0.5 mm and about 13 mm, preferably about 1 mm to about 5 mm.

Another aspect of the present invention is a method of making an absorbable foam by a lyophilization process. This process has the following steps:

a) providing an absorbable polymer comprising a semicrystalline absorbable segmented copolymer, comprising repeating units of polymerized glycolide and polymerized epsilon-caprolactone, wherein the mole ratio of polymerized glycolide to polymerized epsilon-caprolactone is about 55:45 to about 65:35, and wherein the mole ratio of polymerized glycolide to polymerized epsilon-caprolactone in the center block is between about 45:55 to about 60:40;

b) dissolving a sufficient quantity of the copolymer in a suitable solvent to form a lyophilizing solution;

c) pouring at least a part of the solution at a sufficiently effective temperature to prevent premature gel formation into a suitable mold;

d) freezing the solution at a fast enough rate to prevent premature gel formation in order to facilitate solvent removal in a subsequent lyophilization process; and, e) subjecting the frozen solution in the mold to a lyophilizing process, whereby the pressure is lowered and heat is applied to sublimate the solvent and form an absorbable foam.

Yet another aspect of the present invention is a lyophilizing solution. The solution comprises a solvent selected from the group consisting of 1,4-dioxane, a mixture of at least 90 weight percent 1,4-dioxane and no more than 10 weight percent water, and a mixture of at least 90 weight percent 1,4-dioxane and no more than 10 weight percent of an organic alcohol having a molecular weight of less than 1,500 Daltons. In addition, the lyophilizing solution of the present invention comprises about 3 wt. % to about 20 wt. % of a semicrystalline absorbable segmented copolymer, which possesses repeating units of polymerized glycolide and polymerized epsilon-caprolactone, wherein the mole ratio of polymerized glycolide to polymerized epsilon-caprolactone is between about 55:45 to about 65:35, and wherein the mole ratio of polymerized glycolide to polymerized epsilon-caprolactone in the center block between about 45:55 to about 60:40.

Still yet another aspect of the present invention is an annealing process for the above-described lyophilized foams of the present invention. The annealing process allows for fine tuning of the mechanical properties and dimensional stability of the lyophilized foams by exposing the foams to temperatures ranging from about 60° C. to about 110° C. for about 1 to about 12 hours.

These and other aspects and advantages of the present invention will become more apparent from the following description and accompanying drawings.

BRIEF DESCRIPTION OF THE DRAWINGS

FIG. 1 is a schematic representation of the polymers of the present invention.

FIG. 2 is a graphical representation of the compositions of the polymers of the present invention.

FIG. 3 is a graph showing isothermal crystallization curves for selected lots of polymers.

FIG. 4 is a graph showing a primary drying profile for the lyophilization of a random copolymer (CAP/GLY).

FIG. 5 is a graph showing primary drying profile for lyophilization of inventive segmented block copolymer solutions with different gelation times.

FIG. 6 is a graph showing the primary drying profile for lyophilization of inventive segmented block copolymer solutions with different gelation times.

FIG. 7 is a graph showing DSC thermograms of foams based on polymer 5 annealed at various temperatures.

DETAILED DESCRIPTION OF INVENTION

Co-pending, commonly-assigned U.S. patent application Ser. No. 14/728,177 filed on evendate herewith is incorporated by reference.

The terms absorbable, bioabsorbable, bioresorbable, resorbable, biodegradable are used herein interchangeably.

As used herein, and for clarity purposes, a number of terms will be defined. A random (copolyester) copolymer is defined as a copolyester having a sequence distribution of the monomer moieties along the chain that is at least as random as a copolymer of that overall composition made from lactone monomers or hydroxy acids in which all the monomers are added in a single step to the polymerization reactor, as governed by reactivity ratio considerations at the time of the polymerization.

Statistical copolymers are copolymers in which the sequence of monomer residues follows a statistical rule. If the probability of finding a given type monomer residue at a particular point in the chain is equal to the mole fraction of that monomer residue in the chain, then the polymer may be referred to as a "truly random copolymer". In a random copolymer, the sequence distribution of monomeric units follows Bernoullian statistics.

Truly random copolymers are difficult to find due to the complications of the phenomena of monomer reactivity ratios. Although the monomers may be added to a batch reactor in a single step, there may be a slight propensity of one monomer adding to the growing chain over another monomer. This is discussed further below in this specification.

To form a random copolymer in a batch polymerization process, the monomers are generally added to the batch reactor in a single step. In a continuous polymerization process, the monomers are added to the continuous reactor in a substantially constant composition.

A segmented (copolyester) copolymer, on the other hand, possesses a non-random sequence distribution beyond what would be expected based on reactivity ratio considerations that is less random than a random copolymer.

When the sequence length of a given monomer starts to get large, one begins to approach a blocky structure. A "block copolymer" can be multi-block in nature, tetrablock, triblock or diblock, depending on the number of different chemical blocks.

A block copolymer that is a "diblock copolymer" might have a structure containing two different chemical blocks and is then referred to as an A-B block copolymer. If a triblock copolymers has one monomer sequence, A, at its ends and a second, B, in its interior, it might be referred to an A-B-A block copolymer.

A known technique to produce a non-random sequence distribution in ring-opening polymerizations is the method of adding different monomer feeds to the reactor in stages. For example, one might add an amount of monomer B to the reactor with a monofunctional initiator. A polymer is formed made of only B sequences. A second monomer, A, is then added to the reactor; the copolymer thus formed might then be an A-B block copolymer. Alternately, if a difunctional initiator is used at the start of the polymerization, the copolymer thus formed might then be an A-B-A block copolymer.

To help in characterizing the "blockiness" of the sequence distribution of a copolymer, Harwood (reference: Harwood, H. J.; Ritchey, W. M., *Polymer Lett.* 1964, 2, 601) disclosed a "run number" concept. For a copolymer made up of polymerized "A" repeat units and polymerized "B" repeat units, the corresponding run numbers reflect the average chain sequence length for the individual "monomers". In looking down the chain, every time an A unit was encountered, a counter was activated. Every time another A unit was observed, the counter was increased by one; the counter was stopped as soon as a B unit was reached. When the entire chain is sampled and the work completed on the rest of the resin, an average value can be established for the Harwood run number for the "A" unit. The same can be done for "B". Statistical treatments have shown that for a theoretically random copolymer of A/B molar composition, the Harwood run number for each of the components can be calculated based on the following equations:

$$\text{HRN}_A = 1 + ([A]/[B]) \text{ and } \text{HRN}_B = 1 + ([B]/[A]) \qquad (1)$$

where $HRN_A$ and $HRN_B$ are the Harwood Run Numbers for repeat units A and B, respectively, [A] and [B] are the molar fractions of repeat units A and B, respectively.

Thus a 20/80 A/B random copolymer made up of A and B units is expected to have Harwood run numbers of 1.25 and 5.0 for A and B, respectively. In the case of non-random copolymers, it is possible to have a copolymer of the same 20/80 composition with a Harwood run number for the A component much higher than the 1.25 value displayed in the random copolymer, for instance 1.5 or 3. This is clearly indicative of a propensity of "A" units to be together, i.e., a blocky sequence distribution.

In a copolymerization, the monomers may not be sequenced exactly randomly due to a phenomenon in which there is a great propensity of "monomer 1" to add to a growing chain terminated in a "monomer 1 repeat unit" or a great propensity of monomer 1 to add to a growing chain terminated in a "monomer 2 repeat unit". The concept of reactivity ratios, $r_1$ and $r_2$, has been developed to describe the phenomena.

The segmented copolymers useful in the practice of the present invention are semi-crystalline in nature. The segmented copolymers have a center block of more or less random caprolactone and glycolide monomer repeats and terminal end blocks that are comprised predominantly of glycolide monomer (schematically represented in FIG. 1). The prepolymer compositions being in the range of typically about 45/55 to about 60/40 and the final compositions being typically about 55/45 to about 65/35, mole basis, glycolide/ epsilon-caprolactone. It has been surprisingly and unexpectedly discovered that the copolymers useful in the practice of the present invention are semi-crystalline in nature with glass transition temperatures well below room temperature. One particularly preferred application, among other, for such polymers is in the production of novel, strong, soft, dimensionally stable foams.

Poly(glycolide) is a high glass transition temperature ($T_g$ of about 40° C.), semi-crystalline polyester. This material has a high elastic modulus and is thus quite stiff. The high (elastic) modulus exhibited by poly(glycolide) also makes it unsuitable for foams that must be compressible with good recovery; such articles, made from poly(glycolide), are just too stiff. It has been found, however, that certain copolymers of glycolide and epsilon-caprolactone are, surprisingly and unexpectedly, particularly useful for applications requiring softness and compressibility, and, a longer term mechanical property loss profile.

The present invention is directed toward medical devices in the form of foams made from copolymers of glycolide and epsilon-caprolactone and methods of making such constructs. More specifically, this class of copolymers rich in glycolide and made to have a blocky sequence distribution, that is non-random. In such glycolide/epsilon-caprolactone copolymers in which the majority of the material is based on glycolide, the morphology of the resin needs to be optimized to be useful in the present application. We have discovered that the compositions must be rich in glycolide, e.g., having a polymerized glycolide content of 50 percent or greater.

Novel absorbable polymers have been, surprisingly and unexpectedly, discovered having a relatively narrow composition range and a non-random sequence distribution, which when made into foams, will yield foams that are soft enough to have good handling characteristics, yet possess sufficiently effective mechanical integrity in vivo beyond 4 weeks post implantation. Segmented, that is, possessing a non-random sequence distribution beyond what would be expected based on reactivity ratio considerations, poly(glycolide-co-epsilon-caprolactone) copolymers comprising a polymerized glycolide having a molar level between about 55 mole percent to about 65 mole percent and a polymerized epsilon-caprolactone molar level between about 35 mole percent to about 45 mole percent are useful in the practice of the present invention. This class of copolymers, the poly(glycolide-co-epsilon-caprolactone) family rich in glycolide, preferably contains about 35 mole percent to about 45 mole percent of polymerized epsilon-caprolactone.

Specifically, poly(glycolide-co-epsilon-caprolactone) copolymers rich in polymerized glycolide having levels of incorporated glycolide lower than about 55 mole percent are unsuitable for copolymers useful in the practice of the present invention because of crystallization difficulties. On the other hand, poly(glycolide-co-epsilon-caprolactone) copolymers rich in polymerized glycolide having levels of incorporated glycolide greater than about 70 mole percent are unsuitable due to insolubility in solvents suitable for lyophilization.

Dimensional stability of foams, films and nonwoven fabrics used to manufacture surgical devices is very important to prevent shrinkage or warpage, both in the sterile package before use, as well as in the patient after surgical implantation (in vivo). Dimensional stability in a low $T_g$ material can be achieved by crystallization of the formed article. Regarding the phenomena of crystallization of copolymers, a number of factors play important roles. These factors include overall chemical composition and sequence distribution. The dimensional stability of foams of the present invention is related to the ability of these articles to substantially maintain their physical dimensions even when exposed to slightly elevated temperatures, for example 37° C., and/or exposure to plasticizing gases such as ethylene oxide as may occur during sterilization. Although the overall level of crystallinity (and the $T_g$ of the material) plays a role in dimensional stability, it is important to realize that the rate at which the crystallinity is achieved is critical to processing. If a lower $T_g$ material is processed and its rate of crystallization is very slow, it is very difficult to maintain dimensional tolerances since shrinkage and warpage easily occur. Fast crystallization is thus an advantage. It has been discovered that for the systems of the present invention, in order to increase the rate of crystallization of a copolymer of given overall chemical composition, a block structure is preferable over a random sequence distribution. However, surprisingly and unexpectedly, it is now possible to achieve this with two lactone monomers, for instance glycolide and epsilon-caprolactone, notwithstanding experimental difficulties and challenges due to transesterification and other factors.

Useful in the practice of the present invention, the compositional sequence of the inventive semi-crystalline copolymers is schematically illustrated as follows:

GGGGGGGGGGGGGGG-
   GCGCGGCGCGCGGGCGCGGCG-
   GGGGGGGGGGGGGGG
(Polymerized Glycolide Block-Polymerized (Glycolide-co-epsilon-Caprolactone)-Polymerized Glycolide Block)

The semi-crystalline polyglycolide blocks represent approximately about 5 weight percent to about 20 weight percent of the copolymer and the middle block is formed from a nearly amorphous random prepolymer based on polymerized glycolide and epsilon-caprolactone. In the above formula, G represents glycolide, and C represents epsilon-caprolactone.

The novel copolymers useful in the practice of the present invention are prepared by first polymerizing the glycolide and epsilon-caprolactone monomers at temperatures between about 190° C. and about 220° C. Temperatures between about 195° C. and about 205° C. are particularly advantageous and preferred. Although a monofunctional alcohol such as dodecanol might be used for initiation, a diol such as diethylene glycol has been found to work well. Combinations of mono-functional and di-functional, or multifunctional conventional initiators may also be used as a means of further influencing some important characteristics such as morphological development including crystallization rates and ultimate crystallinity levels. Reaction times can vary with catalyst level. Suitable catalysts include conventional catalysts such as stannous octoate. Sufficiently effective amounts of catalyst are utilized. The catalyst may be used at an overall monomer/catalyst level ranging from about 10,000/1 to about 300,000/1, with a preferred level of about 25,000/1 to about 100,000/1. After the completion of this first stage of the polymerization (e.g., about 4 to 8 hours), the temperature is raised to above about 210° C. (typically about 210° C. to 215° C.). Once the temperature is increased, for example to about 215° C., the balance of glycolide monomer can be added to the reactor; this can be conveniently done by pre-melting the monomer and adding it in a molten form. Once the second portion of glycolide monomer is added, the temperature is brought to about 195° C. to about 205° C. in order to complete the co-polymerization for a sufficiently effective time period (e.g., for about 1 to 2 hours).

It will be clear to one skilled in the art that various alternate polymerization approaches and parameters are possible to produce the copolymers of the present invention. For example, although not preferred, it may be possible to conduct all or part of the polymerizations without a catalyst present.

It is to be understood that the monomer feed added to the prepolymer may not necessarily need to be pure glycolide. Instead of adding pure glycolide monomer to the prepolymer, up to about ten mole percent of another monomer may be used to adjust the monomer feed added to the prepolymer. For instance, the monomer feed added to the prepolymer may contain minor amounts of epsilon-caprolactone; the monomer feed might be for example 90/10 glycolide/epsilon-caprolactone. Adding epsilon-caprolactone to the "end blocks" will lower the melting point, crystallization rate and overall crystallinity of the final copolymer. Adding more than about ten mole percent reduces the required properties of the final copolymer too much to be useful for most applications. The compositional sequence of this variant of the inventive semi-crystalline copolymer is schematically illustrated as follows:

GGCGGGGGGGGCGG-
CGCGCCGCGCGCCCGCGCCGC-
GGGGGGGCGGGGGG

Polymerization variations include the possibility of adding the "prepolymer" or "second stage" monomer in multiple steps. Alternately, additional monomer may be added to the formed prepolymer in a continuous fashion over a short period of time, for instance about 10 minutes or over a relatively longer period of time, for instance about 2 hours.

Although adding all of the catalyst at the start of the polymerization is described herein, that is, at the start of the formation of the prepolymer, alternatively only a portion of the catalyst may be added in this stage of the polymerization, adding the remainder later, during the introduction of the monomer to the now formed prepolymer.

It is to be understood that sufficiently effective amounts of acceptable coloring agents such as dyes and pigments might be added at any stage of the polymerization. Such colorants include D&C Violet No 2 or D&C Green No 6. Alternatively, the dye could be introduced during subsequent processing steps such as the lyophilization process.

Again, one skilled in the art can provide a variety of alternate polymerization schemes to provide the novel copolymers of the present invention.

The novel copolymers useful in the practice of the present invention are semicrystalline in nature. They will have a molecular weight sufficiently high to allow the medical devices formed therefrom to effectively have the mechanical properties needed to perform their intended function. For melt blown nonwoven structures and microsphere formation, the molecular weights may be a bit lower, and for conventional melt extruded fibers, they may be a bit higher. Typically, for example, the molecular weight of the copolymers of the present invention will be such so as to exhibit inherent viscosities as measured in hexafluoroisopropanol (HFIP, or hexafluoro-2-propanol) at 25° C. and at a concentration of 0.1 g/dL between about 0.5 to about 2.5 dL/g. More typical inherent viscosities of the copolymer range from about 0.8 dL/g to about 2.0 dL/g with preferred values ranging from about 1.2 dL/g to about 1.8 dL/g, as measured in HFIP at 25° C. and at a concentration of 0.1 g/dL.

In one embodiment, medical devices made of the copolymers of the present invention may contain sufficiently effective amounts of conventional active ingredients or may have coatings containing such ingredients, such as antimicrobials, antibiotics, therapeutic agents, hemostatic agents, radio-opaque materials, tissue growth factors, and combinations thereof. In one embodiment the antimicrobial is Triclosan, PHMB, silver and silver derivatives, or any other bio-active agent.

The variety of therapeutic agents that may be used is vast. In general, therapeutic agents which may be administered via these medical devices and compositions of the present invention include, without limitation, antiinfectives, such as antibiotics and antiviral agents; analgesics and analgesic combinations; anorexics; antihelmintics; antiarthritics; antiasthmatic agents; adhesion preventatives; anticonvulsants; antidepressants; antidiuretic agents; antidiarrheals; antihistamines; anti-inflammatory agents; antimigraine preparations; contraceptives; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, hemostatics, clot dissolving agents, radioactive agents and cystostatics. Therapeutically effective dosages may be determined by in vitro or in vivo methods. For each particular additive or active ingredient, individual determinations may be made to determine the optimal dosage required. The determination of effective dosage levels to achieve the desired result will be within the realm of one skilled in the art. The release rate of the additives or active ingredients may also be varied within the realm of one skilled in the art to determine an advantageous profile, depending on the therapeutic conditions to be treated.

The copolymers of the subject invention can be melt extruded by a variety of conventional means. Monofilament fiber formation can be accomplished by melt extrusion followed by extrudate drawing with or without annealing. Multifilament fiber formation is possible by conventional means. Methods of manufacturing monofilament and multifilament braided sutures are disclosed in U.S. Pat. No. 5,133,739, entitled "Segmented Copolymers of epsilon-Caprolactone and Glycolide" and U.S. Pat. No. 6,712,838 entitled "Braided. Suture with Improved Knot Strength and Process to Produce Same", which are incorporated by reference herein in their entirety.

The copolymers of the present invention may be used to manufacture conventional medical devices in addition to sutures using conventional processes. For example, injection molding may be accomplished after allowing the copolymer to crystallize in the mold; alternately, biocompatible nucleating agents might be added to the copolymer to reduce cycle time. The copolymers of the present invention may be used to manufacture medical devices that function in part by being deformable without undergoing significant fracturing, cracking, splintering or other forms of breakage. Medical devices that function in part by being deformable include those that have hinges or are required to bend substantially. The medical devices may include (but are not limited to), conventional medical devices, especially implantable medical devices, including staples, tacks, clips, sutures, barbed sutures, tissue fixation devices, mesh fixation devices, anastomosis devices, suture and bone anchors, tissue and bone screws, bone plates, prostheses, support structures, tissue augmentation devices, tissue ligating devices, patches, substrates, meshes, tissue engineering scaffolds, drug delivery devices, and stents, etc.

The copolymers of the present invention may be used to produce inter-connected open cell porous foams by lyophilization. The lyophilization process is described as first dissolving the copolymers in a suitable solvent to prepare a homogeneous solution. The concentration of the polymer solution (i.e., lyophilization solution) of the present invention ranges from about 3 weight percent to about 20 weight percent, more preferably from about 5 weight percent to about 15 weight percent. Next, the lyophilization solution is subjected to a cooling thermal treatment that freezes the solution in order to achieve phase separation between the polymer and solvent components, and locks in the pore morphology. It should be appreciated by those skilled in the art, that the solvent crystals form the eventual pores of the foam. The frozen polymer-solvent system then undergoes a vacuum drying cycle that removes the solvent by sublimation leaving the porous polymer structure. The vacuum drying cycle is typically performed at multiple temperatures. "Primary drying" occurs by sublimation at a temperature below the freezing point of the solvent; bulk solvent removal occurs during this process. Often a "secondary drying" above the freezing point of the solvent is used to remove any residual bound solvent by evaporation. It is advantageous to remove the majority of solvent during primary drying. The reason for this is because at temperatures above the freezing point of the solvent any significant amounts of remaining solvent could re-dissolve the polymer and disrupt the porous structure of the foam. This phenomena is often referred to as "melt-back" and can result in a product having a warped or "potato chip"-like appearance.

The solvents used for lyophilization should be selected for suitability for lyophilization (appropriate freezing temperatures, vapor pressure, etc.) and adequate polymer solubility. Solvents suitable for lyophilization include but are not limited to solvents selected from a group consisting of water, formic acid, ethyl formate, acetic acid, hexafluoroisopropanol (HFIP), cyclic ethers (i.e. TMF, DMF, and PDO), acetone, acetates of C2 to C5 alcohol (such as ethyl acetate and t-butylacetate), glyme (i.e. monoglyme, ethyl glyme, diglyme, ethyl diglyme, triglyme, butyl diglyme, and tetraglyme), methyl-ethyl ketone, dipropyleneglycol methyl ether, lactones (such as γ-valerolactone, δ-valerolactone, β-butyrolactone, γ-butyrolactone), 1,4-dioxane, 1,3-dioxolane, 1,3-dioxolane-2-one (ethylene carbonate), dimethylcarbonate, benzene, toluene, benzyl alcohol, p-xylene, naphthalene, tetrahydrofuran, N-methyl pyrrolidone, dimethylformamide, chloroform, 1,2-dicholromethane, morpholine, dimethylsulfoxide, hexafluoroaceteone sesquihydrate (HFAS), anisole and mixtures thereof. Among these solvents, the preferred solvent in the practice of the present invention is 1,4-dioxane.

The polymer solution is typically dispensed into a mold prior to lyophilization for two purposes: 1) to provide containment of the liquid polymer solution for thermal treatment and 2) to provide a template for the shape of the resulting foam. The fill depth of the solution directly correlates to the thickness of the foam whereby the preferred resulting thickness for the foams of the present invention ranges from about 0.5 mm to about 13 mm. The mold is required to have an opening to permit sublimation of the solvent. The mold can be made of any material that is compatible with the solvent system in order to maintain mold integrity throughout the process. It is often preferred that the mold be made of a material with a high thermal conductivity to facilitate the heat transfer to the polymer solution for the thermal treatment. The preferred mold materials for the present invention include aluminum and stainless steel but one skilled in the art would also appreciate that a wide variety of conventional materials can be used.

Most bioabsorbable polymers are poorly soluble in the solvents suitable for lyophilization. Surprisingly, polymer solutions at concentrations resulting in foams with desirable bulk densities can be made with the copolymers of the present invention. Certain of these lyophilization solutions were unexpectedly found to form undesirable gels at a fast rate. Once a gel is formed, it is very difficult for polymer chains to possess the mobility they need for phase separation that must occur as the pure solvent crystallizes. The solvent is then trapped in these "fixed" chains, thus making it very difficult for the solvent to be removed by sublimation. It has been found that no parameters in primary drying (temperature, pressure, or time) were effective in the solvent removal from a gelled polymer solution. Furthermore, exposing the gels to thermal treatments (heating, cooling, and heat/cool cycles) were also found to be unsuccessful to enable drying of the solvent. The only successful approach found for lyophilizing these polymer solutions was to quickly freeze the solution before the undesirable gels could form and thus preventing the solvent from being trapped within the gel.

Freezing of the polymer solution needs to occur at a faster rate than the time needed for gel formation; however it should be appreciated that the kinetics of gelation increases with lower temperatures, as temperature will also affect the mobility of the polymer chains. As the temperature of the solution decreases, the onset time to gelation increases. The preferred cooling rates for the initial thermal treatment of the preferred embodiment of this invention is equal or faster than 5° C./min (−5° C./min when considered as a temperature rate). A more preferred cooling rate is equal or faster than 10° C./min (−10° C./min when considered as a temperature rate).

There can be a number of methods to achieve the above mentioned cooling rates which can incorporate many factors such as the amount of solution to be frozen; the depth of solution to be frozen; mold design; convective and conductive thermal transfer; and, heat transfer aids such as cold fingers. The preferred method of the present invention is to utilize a "quench" wherein the polymer solution (in a mold) is introduced into an extremely cold environment, typically below −30° C., such as cold shelves in a lyophilization unit, a refrigerator, a liquid nitrogen or other coolant bath, or a liquid nitrogen cooled flash freezer. The solution can also be poured directly into a pre-chilled mold where it will be exposed to the cold environment immediately; however this can impact the ability of the solution to completely fill the mold. Thermocouples can be used to monitor the solution temperature and define the appropriate conditions to achieve the desired cooling rate of at least 5° C./min.

After the initial freezing of polymer solution before undesirable gelation can form, the frozen polymer-solvent system can optionally undergo further thermal treatment. This can include a step wherein the temperature is raised above the Tg', which is known as the glass transition temperature of the lyophilization solution, but below its freezing temperature to normalize the solvent ice crystal size through Ostwald ripening. It is critical to not go above the freezing temperature of the solution as the solvent can melt and solubilize the polymer, enabling the opportunity for an undesirable gel to form.

The lyophilization processes of the present invention may be carried out in a conventional tray-style freeze dryer (also known as a lyophilization unit). The units may comprise a cabinet with several shelves that can be heated and cooled by a refrigeration system. These shelves enable heating and cooling for the thermal treatment and drying cycles typically providing a shelf temperature range from −70° C. to 60° C. The interior of the cabinet of the lyophilization unit is connected directly to a vacuum pump that reduces the ambient gas pressure in the cabinet and a condenser that collects the solvent vapor that is sublimated from the product on a surface that is typically cooled to −40° C. to −80° C. It is preferred that the lyophilization unit has equipment to aid the determination of the end point of primary drying such as product thermocouples, comparative pressure measurement (Pirani vs. capacitance manometer), dew point, pressure rise test, and other as described by Patel et al., *AAPS PharSciTech*, 11, 2010. It should be appreciated by those skilled in the art that lyophilization could be performed in other conventional freeze dryer configurations including manifold and rotary freeze dryers.

The polymeric foams generated in this invention have interconnected and open cell porous structures. Foam density is directly associated with the concentration of the polymer solution and can typically range from about 50 mg/cc to about 300 mg/cc. The foams possess a solids content between about 3 weight percent and about 20 weight percent, preferably between about 5 weight percent and about 15 weight percent. The preferred thickness of the foams of the present invention ranges from about 0.5 mm to about 13 mm, preferably between about 1 mm to about 5 mm.

The foams made from the copolymers of the present invention may be used in medical applications as scaffolds for tissue engineering, buttress materials, defect or space fillers, wound healing dressing, 3D devices such as porous grafts, and other implantable wound healing, augmentation, and regeneration devices. The foams may be used in combination with other devices (such as meshes and other textiles) or additives that can be added during the lyophilization process. The foams may also be used as a drug delivery matrix whereby a therapeutic agent is mixed into the polymer solution before forming the foam or loaded into the foam after it is formed.

It has been found that the foam parts made from the copolymers of the present invention exhibit excellent dimensional stability during manufacture, during ethylene oxide sterilization, and upon storage of packaged products.

Additionally, it has been found that at a given bulk density, the copolymers of the present invention provide higher mechanical properties at a given foam bulk density due to the higher crystallinities that are achievable with these resins.

Most importantly, however, it has been found that the inventive foams of the present application degrade at a slower rate than those of Vyakarnam, et al. The extended mechanical property loss profiles exhibited post-implantation are very important in certain key surgical procedures. To be clear, the Vyakarnam, et al. foams exhibit zero residual strength under compression at approximately 25 days of in vitro treatment at 37° C. and pH 7.27, while the foams of the present invention last for a period of time equal to or longer than 40 days.

It has been further found that both the dimensional stability and mechanical properties of the foams of the present invention can be optimized utilizing a thermal treatment process step post-lyophilization (i.e. annealing). It was surprising and unexpected that annealing at a higher temperature resulted in foams with more 'spring-back' or recovery of compressive force after being compressed to 1.0 mm. However, when annealed at too high a temperature (e.g. 120° C.), the resulting foams lost their mechanical properties faster while undergoing hydrolytic degradation than those annealed at lower temperatures. There is thus a balance to be found that can be refined depending on the desired application. The preferred annealing temperature for the foams of the present invention is from about 60° C. to about 110° C., preferably from about 70° C. to about 100° C., and more preferably from about 85° C. to about 95° C. The duration of the annealing process is from about 1 hour to about 12 hours, preferably from about 4 hours to about 8 hours.

In summary, the foams of the present invention exhibit the numerous advantages over the prior art foams. The advantages include that foams of the present invention display higher mechanical properties due both to the higher crystallinities that are achievable at a given foam bulk density [based on the solids content of the solution to be lyophilized]; good dimensional stability of the foam parts during manufacture, ethylene oxide sterilization, and storage; and extended mechanical property loss profiles exhibited post-implantation.

The following examples are illustrative of the principles and practice of the present invention, although not limited thereto:

EXAMPLES

Example 1

Synthesis of Random Copolymers of ε-Caprolactone and Glycolide (Control)

Using a conventional 10-gallon stainless steel oil-jacketed reactor equipped with agitation, 9,153 grams of epsilon-caprolactone and 15,848 grams of glycolide were added along with 25 mL of diethylene glycol and 14.6 mL of a 0.33M solution of stannous octoate in toluene. After the initial charge, a purging cycle with agitation at a rotational speed of 8 RPM in a downward direction was initiated. The reactor was evacuated to pressures less than 1 Torr followed by the introduction of nitrogen gas. The cycle was repeated twice again to ensure a dry atmosphere. At the end of the final nitrogen purge, the pressure was adjusted to be slightly above one atmosphere. The vessel was heated by setting the oil controller at 190° C. When the batch temperature reached 140° C., rotation of the agitator was switched to an upward direction and the speed increased to 15 RPM. After two hours of reaction at 190° C., the agitation was reduced to 8 RPM. The reaction continued for 18 hours from the time the oil temperature reached 190° C. after which the temperature was raised to 215° C. The reaction proceeded an additional 2.5 hours at this temperature prior to the discharge.

At the end of the final reaction period, the agitator speed was reduced to 5 RPM in the downward direction, and the polymer was discharged from the vessel into suitable containers. Upon cooling, the polymer was removed from the containers and placed into a freezer set at approximately −20° C. for a minimum of 24 hours. The polymer was then removed from the freezer and placed into a Cumberland granulator fitted with a sizing screen to reduce the polymer granules to approximately 3/8 inches in size. The ground polymer was then placed into a Patterson-Kelley tumble dryer to remove any residual monomer.

The Patterson-Kelley tumble dryer was closed, and the pressure was reduced to less than 200 mTorr. Once the pressure was below 200 mTorr, the dryer rotation was activated at a rotational speed of 10 RPM with no heat for 16 hours. After the 16 hour period, the oil jacket temperature was set to 110° C. with drying at this temperature for 24 hours. At the end of the final heating period, the batch was allowed to cool to room temperature while maintaining rotation and vacuum. The polymer was discharged from the dryer by pressurizing the vessel with nitrogen, opening the discharge valve, and allowing the polymer granules to descend into waiting vessels for long term storage. The long term storage vessels were air tight and outfitted with valves allowing for evacuation so that the resin was stored under vacuum.

Example 2

Synthesis of Inventive Segmented Block Copolymer Poly (ε-Caprolactone-Co-Glycolide).

Using a conventional 2-gallon stainless steel oil-jacketed reactor equipped with agitation, 2,376 grams of epsilon-caprolactone and the desired grams of glycolide (see Table 1) were added along with 3.95 mL of diethylene glycol and 3.50 mL of a 0.33M solution of stannous octoate in toluene. After the initial charge, a purging cycle with agitation at a rotational speed of 15 RPM in a downward direction was initiated. The reactor was evacuated to pressures less than 1 Torr followed by the introduction of nitrogen gas. The cycle was repeated twice again to ensure a dry atmosphere. At the end of the final nitrogen purge, the pressure was adjusted to be slightly above one atmosphere. The vessel was heated by setting the oil controller at 198° C. When the batch temperature reached 135° C., rotation of the agitator was switched to an upward direction and the speed increased to 25 RPM. Once the batch reached 198° C., the temperature was raised to 205° C. and the first monomer addition was made (see Table 1 for details). The rotation of the agitator was switched to a downward direction for ten minutes after which rotation was returned to an upward direction and the temperature lowered to 198° C. One hour after the first addition, the second addition was made following the same method. After two hours of reaction the agitator speed was lowered to 20 rpm and the reaction continued for 4 hours.

After the completion of the first stage portion of the polymerization, a very small amount of resin was discharged for analysis purposes; selected characterization was performed. Then the temperature was raised to 205° C. and the final amount of glycolide monomer was added to create the glycolide end blocks. After ten minutes the temperature was lowered to 198° C. and the reaction was continued for an additional two hours.

At the end of the final reaction period, the agitator speed was reduced to 5 RPM in the downward direction, and the polymer was discharged from the vessel into suitable containers. Upon cooling, the polymer was removed from the containers and placed into a freezer set at approximately −20° C. for a minimum of 24 hours. The polymer was then removed from the freezer and placed into a Cumberland granulator fitted with a sizing screen to reduce the polymer granules to approximately 3/16 inches in size. The ground polymer was then placed into a Patterson-Kelley tumble dryer to remove any residual monomer.

The Patterson-Kelley tumble dryer was closed, and the pressure was reduced to less than 200 mTorr. Once the pressure was below 200 mTorr, the dryer rotation was activated at a rotational speed of 10 RPM with no heat for 10 hours. After the 10 hour period, the oil jacket temperature was set to 80° C. with drying at this temperature for 32 hours. At the end of the final heating period, the batch was allowed to cool to room temperature while maintaining rotation and vacuum. The polymer was discharged from the dryer by pressurizing the vessel with nitrogen, opening the discharge valve, and allowing the polymer granules to descend into waiting vessels for long term storage. The long term storage vessels were air tight and outfitted with valves allowing for evacuation so that the resin was stored under vacuum.

TABLE 1

Monomer Quantities for Each Addition Step

| Polymer | Initial Cap Charge (g) | Initial Gly Charge (g) | First Gly Addition (g) | Second Gly Addition (g) | Final Gly Addition (g) |
| --- | --- | --- | --- | --- | --- |
| 1 | 2196 | 500 | 1300 | 900 | 1103 |
| 2 | 2196 | 900 | 1500 | 903 | 500 |
| 3 | 2196 | 900 | 1200 | 903 | 800 |
| 4 | 1779 | 900 | 1500 | 921 | 900 |
| 5 | 2376 | 900 | 1000 | 924 | 800 |
| 6 | 2376 | 700 | 924 | 900 | 1100 |
| 7 | 2675 | 900 | 1000 | 625 | 800 |
| 8 | 2376 | 900 | 1150 | 924 | 650 |
| 9 | 2376 | 900 | 2224 | | 500 |

Example 3

Selected Data for Cap/Gly Polymers

Molecular weights of the polymers of Examples 1 and 2 were determined using Gel Permeation Chromatography at a concentration of 2 mg/mL in hexafluoroisopropanol. The inherent viscosity was measured in hexafluoroisopropanol at 25° C. and at a concentration of 0.10 g/dL. Compositional analysis was performed utilizing $^1$H-NMR spectroscopy (using a Varian 400 MHz NMR system) to experimentally determine residual monomer levels and an average chain sequence length, ASL for caproyl and glycoyl blocks (ASL (C) and ASL(G), respectively). The peak assignments and method analysis used were based on the work reported earlier on a similar class of copolymers (Z. Wei et al./ Polymer 50 (2009) 1423-1429). Thermal analysis was performed using a model Q20-3290 calorimeter from TA Instruments equipped with automatic sampler at a scan speed of 10° C./min.

Table 2 (graphically represented in FIG. 2) shows that at a given composition the average sequence length of caprolactone, increases with increasing block length. Given that with increasing block length and constant composition there will be less glycolide monomer available to co-polymerize with, the randomness of the center block will actually go down. For the same reason, at a given block length, the average sequence length of caprolactone will go up with increasing caprolactone content in the overall composition. The glycolide sequence length increases, as expected, with increasing glycolide end block length and increasing glycolide content in the overall composition.

TABLE 2

Selected Analytical Data for End Block-Containing Copolymers of Caprolactone and Glycolide

| Polymer | Center block Composition (Cap/Gly) | Overall Composition Cap/Gly | IV (dl/g) | Molecular Weight (g/mol) | ASL (C) | ASL (G) |
|---|---|---|---|---|---|---|
| Control | 36/64 | 36/64 | 1.41 | 61,200 | 1.167 | 1.776 |
| 1 | 45/55 | 36/64 | 1.41 | 62,200 | 1.506 | 2.174 |
| 2 | 40/60 | 36/64 | 1.41 | 63,700 | 1.27 | 1.931 |
| 3 | 43/57 | 36/64 | 1.34 | 59,000 | 1.357 | 2.042 |
| 4 | 35/65 | 30/70 | 1.37 | 60,800 | 1.227 | 2.466 |
| 5 | 46/54 | 40/60 | 1.51 | 64,500 | 1.342 | 1.801 |
| 6 | 49/51 | 40/60 | 1.53 | 65,600 | 1.368 | 1.822 |
| 7 | 52/48 | 45/55 | 1.40 | 53,400 | 1.45 | 1.581 |
| 8 | 45/55 | 40/60 | 1.30 | 55,800 | 1.32 | 1.742 |
| 9 | 44/56 | 40/60 | 1.53 | 65,800 | 1.354 | 1.796 |

* ASL = average sequence length, C = caprolactone, G = glycolide

*ASL=average sequence length, C=caprolactone, G=glycolide

It is evident from Table 3 that the inventive polymers of the present invention exhibit substantially higher levels of crystallinity (as estimated by the heat of fusion of the first heat) than the prior art control polymer. Similarly, the second heat data shows that substantially more crystallinity develops in the glycolide end block containing polymers in the time frame of the cooling run.

TABLE 3

Selected Thermal Data for End Block-Containing copolymers of Caprolactone and Glycolide

| | First heat | | | Second heat | | |
|---|---|---|---|---|---|---|
| Polymer | $T_g$ (° C.) | $T_m$ (° C.) | $\Delta H_m$ (J/g) | $T_g$ (° C.) | $T_m$ (° C.) | $\Delta H_m$ (J/g) |
| Control | −11.4 | 118.4 | 23.3 | −7.1 | 115.5 | 1.01 |
| 1 | −16.9 | 155.4 | 29.0 | −15.1 | 145.2 | 33.5 |
| 2 | −13.1 | 123.5 | 30.2 | −8.1 | 114.8 | 14.5 |
| 3 | −10.5 | 148.4 | 35.3 | −9.9 | 144.7 | 31.9 |
| 4 | −8.8 | 158.4 | 47.3 | −4.11 | 154.3 | 35.5 |
| 5 | −18.0 | 132.4 | 35.9 | −13.5 | 140.7 | 25.5 |
| 6 | −17.8 | 133.8 | 34.2 | −13.0 | 141.0 | 24.8 |
| 7 | −24.8 | 136.1 | 30.3 | −20.0 | 136.5 | 14.8 |
| 8 | −19.4 | 123.7 | 36.7 | −15.6 | 133.7 | 20.5 |
| 9 | −15.3 | 129.6 | 32.4 | −10.2 | 120.8 | 13.7 |

It is very important to note that in all cases only a single $T_g$ is observed after the first heating scans. The $T_g$ values were all well below room temperature, ranging from −9° C. to −25° C.; low $T_g$ values may contribute to increased softness of medical devices produced from these materials.

Example 4

Effect of Composition and End Block on Rate of Crystallization

Isothermal crystallization kinetics of the polymers of the present invention were evaluated using differential scanning calorimetry. The dried resins, as described in Examples 1 and 2 were placed into a DSC pan and completely melted at 190° C. for 2 minutes to remove any nucleation sites present in the sample. Subsequently, tested materials were rapidly cooled/quenched (rate −65° C./min) to the desired crystallization temperatures. The isothermal method assumes that no crystallization occurs before the sample reaches the test temperature; the data obtained supported this assumption. Crystallization behavior of the five samples was characterized over a wide range of temperatures, between 50° C. and 90° C. Isothermal crystallization kinetics (at constant temperature) was monitored as a change in heat flow as a function of time. The isothermal heat flow curve was integrated to determine the crystallinity parameters.

After performing the integration of the heat flow/time curve, the crystallization half-time, $t_{1/2}$, can be determined. The crystallization half-time is the time needed to reach 50 percent crystallinity of the total amount developed during the isothermal run. In order to express crystallization kinetics, a reciprocal crystallization half-time was presented as a function of crystallization temperature. These data are shown graphically in FIG. 3. It is evident from the graph that the inventive polymers crystallize between 2 to 5 times faster than the control polymer from the prior art. It can also be seen that crystallization is more rapid with increasing end block length. Finally, there is a dependence on composition. Polymer 3 was also evaluated but crystallized fully upon cooling from the melt to the selected temperatures.

Example 5

Solubility

The maximum solubility of a resin in 1,4-dioxane was tested by an incremental addition approach. To start, 10 g of resin was added to 100 mL of 1,4-dioxane in a 250 mL in a round bottom flask. The flask with the solution was placed on a water bath heated to 85° C. and fitted with an inlet adapter connected to a nitrogen line. After dissolution, resin was added in 1 g increments until either the resin did not fully dissolve within 2 hours or gelation occurred.

Table 4 demonstrates that with increasing glycolide end block length, the solubility in 1,4-dioxane decreases. Furthermore, solubility decreases with increasing glycolide content in the overall composition. In fact, Polymer 4 is not soluble at relevant concentrations (<0.5 wt %).

TABLE 4

Selected Solubility and Onset of Gelation Data for End Block-Containing Copolymers of Caprolactone and Glycolide

| Polymer | Center Block Composition (Cap/Gly) | Overall Composition Cap/Gly | Max. Solubility (g/100 ml) | Onset of Gelation (Minutes) |
|---|---|---|---|---|
| Control | 36/64 | 36/64 | 24 | >180 |
| 1 | 45/55 | 36/64 | 8 | 19 ** |
| 2 | 40/60 | 36/64 | 25 | 78 |

TABLE 4-continued

Selected Solubility and Onset of Gelation Data for End Block-Containing Copolymers of Caprolactone and Glycolide

| Polymer | Center Block Composition (Cap/Gly) | Overall Composition Cap/Gly | Max. Solubility (g/100 ml) | Onset of Gelation (Minutes) |
|---|---|---|---|---|
| 3 | 43/57 | 36/64 | 14 | 14 |
| 3 | 43/57 | 36/64 | 14 | 53 ** |
| 4 | 35/65 | 30/70 | <0.5 | N/A |
| 5 | 46/54 | 40/60 | 19 | 113 |
| 6 | 49/51 | 40/60 | 16 | 107 |
| 7 | 52/48 | 45/55 | >25 | >180 |
| 8 | 45/55 | 40/60 | ??? | >180 |
| 9 | 44/56 | 40/60 | 21 | >180 |

** At a concentration of 6 weight %

Example 6

Gelation

All polymers of the present invention, as well as the prior art control polymer, formed organogels within 18 hours after being allowed to cool to room temperature. The onset time of gelation was determined using a Brookfield viscometer. First, 150 mL solution of the selected resin at the desired final concentration in 1,4-dioxane was prepared as described in example 5 (10 percent by weight unless described otherwise). Of this solution, 125 mL was transferred to a narrow 200 mL glass beaker positioned in a 20° C. water bath. Next, a S61 spindle was immersed into the solution and subsequently connected to a zeroed Brookfield DVI-I+ viscometer. Solution viscosity at 10 rpm was monitored and recorded at regular intervals. The onset of gelation time was determined by detecting the point where the viscosity started to increase rapidly. For the purposes of the foam manufacturing process an onset of gelation time greater than 180 minutes was deemed irrelevant.

Four polymers formed organogels sufficiently slow to have no impact on the lyophilization process. These comprise the prior art control polymer, the polymer with a 45/55 Cap/Gly composition, and the two polymers with the shortest glycolide end blocks having a 40/60 Cap/Gly overall composition. The other polymers demonstrated a strong dependence on overall caprolactone content and a secondary dependence on glycolide end block length. In addition, there appeared to be an exponential relationship with both temperature and molecular weight, in which gelation occurred faster at lower temperature and higher molecular weight.

Example 7

Lyophilization Process for Resin of Example 1 (Random Copolymers)

a) Solution Preparation

Solutions were prepared by weighing out 40 grams of the polymer of Example 1 and 360 grams of anhydrous 1,4-dioxane to achieve a 10% (w/w) solution concentration. The two components were combined in an Erlenmeyer flask, which was then fitted with a stir bar and placed in a water bath. The solution was heated at 70° C. with agitation for 1 to 2 hours. After removal from heat, the solution was then filtered through an extra course filter under gentle nitrogen pressure.

A sample of the solution was then taken to measure the concentration via dry weight measurement. After recording the weight of the solution, the 1,4-dioxane was removed by allowing it to evaporate overnight and then subsequently dried in a vacuum oven heated to 50° C. for 48 hrs. The concentration of the solution was measured to be 10.4% (w/w).

b) Lyophilization

Lyophilization of the polymer solution into a foam construct was carried out in a LyoStar3 unit manufactured by SP Scientific.

Prior to lyophilization, the solution was heated to 75° C. for approximately 1 hour. The hot polymer solution was dispensed into a stainless steel mold having 30 cavities; each cavity had a configuration of a strip that was approximately 10 mm×60 mm×3 mm. The lyophilization cycle was then initiated as specified by a computer utilizing computer-controlled process steps (recipe). The recipe was comprised of the following sequences:

1. Thermal Treatment: The filled mold was placed into the lyophilization unit chamber that was set to a temperature of 15° C. The chamber was held at 15° C. for 30 min and then ramped to −10° C. at a rate of 2° C./min. The shelf temperature was then cooled at a rate of 0.5° C./min until −45° C. for a hold of 1 hr. The temperature was increased to 3° C. at a rate of 1° C./min and the unit was then held at 3° C. for 1 hr. It was then ramped back to −45° C. at a rate of −0.5° C./min for a hold of 1 hr.
2. Evacuation then commenced by pulling vacuum to 450 mTorr. Once that level was achieved, the unit was held at −45° C. for 2 hours.
3. Primary drying was then started by ramping the unit to −10° C. at a rate of 0.5° C./min and held for 5 hours. The vacuum level was then decreased to 20 mTorr and the shelf temperature was increased to 10° C. at a rate of 0.25° C./min and held for 3 hours. The shelf temperature was then increased to 20° C. at a rate of 2° C./min and kept at that level until the cycle was stopped and vacuum was broken with nitrogen.

The lyophilization unit was equipped with a Pirani vacuum gauge, which was used to assess the primary drying time during lyophilization via comparative pressure measurement with a capacitance manometer (CM) (Patel S M et al., AAPS PharmSciTech, 11, 2010). Briefly, the CM measures the absolute pressure in the chamber (the vacuum setpoint) while the Pirani gauge works on the principle of measuring the thermal conductivity of the solvent vapor in the chamber. During sublimation when solvent vapor is present, the Pirani gauge will read higher than the CM. When there is no more vapor in the chamber, the Pirani reading will be the same as CM. A simple visual confirmation is when the two curves intersect during primary drying as shown for this lyophilization run in FIG. 4.

Following lyophilization, the foam strips were removed from the molds and stored under nitrogen until further use.

Example 8

Lyophilization of a Gelled Polymer Solution

In this experiment, using a polymer solution made with a resin that had a fast onset of gelation (Polymer 3 from Example 2), efforts were made to develop a lyophilization recipe to produce uniform foam with low residual solvents. A number of lyophilization parameters were modified in attempts to successfully lyophilize the polymer solution.

a) Solution Preparation

Solutions were prepared by weighing out the polymer (Polymer 3 from Example 2) and anhydrous 1,4-dioxane to achieve a 10% (w/w) solution concentration. The two components were combined in an Erlenmeyer flask, which was then fitted with a stir bar and placed in a water bath. The solution was heated at 85° C. with agitation for 1 to 2 hours. After removal from heat, the solution was then filtered through an extra course filter under gentle nitrogen pressure. The filtered solution was then stored covered at room temperature until use.

b) Lyophilization

Prior to lyophilization, the solution was heated to 75° C. for approximately 1 hour. The hot polymer solution was dispensed into a stainless steel mold having 30 cavities; each cavity had a configuration of a strip that was approximately 10 mm×60 mm×3 mm. The lyophilization cycle was then initiated as specified by computer controlled process steps (recipe). The baseline recipe for this experiment was comprised of the following sequences:

1. Thermal Treatment: The filled mold was placed into the lyophilization unit chamber that was present to a temperature of 15° C. The chamber was held at 15° C. for 30 min and then ramped to −10° C. at a rate of 2° C./min. The shelf temperature was then cooled at a rate of 0.5° C./min until −45° C. for a hold of 1 hour. The temperature was increased to 3° C. at a rate of 1° C./min and the unit was then held at 3° C. for 1 hour. It was then ramped back to −45° C. at a rate of −0.5° C./min for a hold of 1 hour.
2. Evacuation then commenced by pulling vacuum to 450 mTorr. Once that level was achieved, the unit was held at −45° C. for 2 hours.
3. Primary drying was then started by ramping the unit to −10° C. at a rate of 0.5° C./min and holding for 5 hours. The vacuum level was then decreased to 20 mTorr and the shelf temperature was increased to 10° C. at a rate of 0.25° C./min and held for 3 hours. The shelf temperature was then increased to 20° C. at a rate of 2° C./min and kept at that level until the cycle was stopped and vacuum was broken with nitrogen.

The recipe was then modified with the following parameters for these experiments as described in Table 5:

TABLE 5

Modification to Baseline Recipe for Development of Lyophilization Recipe for a Gelled Polymer Solution

| Modification | Description of Change from Baseline Recipe |
| --- | --- |
| 1 | Mold loaded onto shelf at 15° C. and cooled down to −45° C. at a rate of 0.2° C./min and held for 5 hrs.; Primary dry time extended from 5 hrs. to 48 hrs. |
| 2 | Mold loaded onto shelf at 40° C. and cooled down to −10° C. at a rate of 2° C./min |
| 3 | Primary dry temperature decreased to −20° C. |
| 4 | Eliminated thermal treatment after the initial hold at −45° C.; Primary dry temperature decreased to −20° C. and extended from 5 hrs to 12 hrs. |
| 5 | Primary dry temperature increased to 0° C. |
| 6 | Primary dry temperature increased to 5° C. |
| 7 | Primary dry temperature increased to 10° C. |
| 8 | Primary dry temperature increased to 15° C. |
| 9 | Primary dry temperature increased to 5° C.; Primary dry vacuum level decreased to 100 mTorr |
| 10 | Mold loaded onto shelf at −45° C. |

The lyophilization unit was equipped with a Pirani vacuum gauge, which was used to assess the primary drying via comparative pressure measurement with a capacitance manometer (CM). The foam was considered dry when the Pirani curve intersected with the CM curve. Foams were also visually inspected after lyophilization.

c) Results and Discussion

Within the scope of the experiment in this Example, lyophilization of a gelled polymer solution was not successful. With a number of adjustments to various lyophilization parameters, foams were produced, however the foams had a bad visual appearance and high levels of residual solvent. In Modification 1, a slow cooling rate was used to ensure gelation occurred and the freezing and primary drying times were extended while maintaining the same temperatures and pressures as the baseline recipe. This run yielded failed foams that could not be removed from the molds and had a strong odor of 1,4-dioxane indicating that solvent still remained in the product. The results indicated that extending the time for the parameters of the baseline recipe would not effectively lyophilize a gelled solution and that variables other than holding time must be manipulated moving forward.

Modification 2 was another attempt to produce a foam whereby the shelf load temperature was increased to 40° C. as a way to slow down the solution from gelling and then quickly cooled with a shelf cooling rate of 2° C./min. The resulting foams had a strong odor and poor appearance, and, the CM and Pirani curves did not intersect. This suggests that the higher shelf load temperature and the controlled cooling rate of the shelf did not prevent gelation. Most likely, it is believed that the solution began to gel as the solution cooled at a slower rate than the shelf as the cold temperature had to transfer from the shelf through the mold and then through the solution.

Modifications 3 and 4, wherein the primary dry temperature was decreased to −20° C. and the thermal treatment was either included or excluded, did not have an effect on drying the gelled solution. The primary drying profiles were nearly identical, and both runs resulted in failed foams that could not be removed from the molds as well as a strong 1,4-dioxane odor.

Increasing primary drying temperature was evaluated in Modifications 5, 6, 7, and 8 with the thought that it would increase sublimation from the frozen gel. At a primary drying temperature greater than 10° C., removal of dioxane was improved whereby the odor of 1,4-dioxane was not detected and the Pirani curve was approaching closer to the CM curve; however, the temperature was high enough that it caused a structural collapse or "melt-back" of the foam wherein the bottom portion of the foam had a film-like appearance. Based on this result, manipulation of the primary drying temperature alone was not a feasible method for lyophilization of a gelled solution.

Modification 9 used the highest primary drying temperature which did not result in product collapse, 5° C., along with a lower pressure during primary drying. It was thought that a lower chamber pressure during primary drying would help increase the difference between chamber pressure and vapor pressure of the solvent in the gel, therefore increasing the driving force for sublimation. The resulting CM and Pirani curves did not intersect before the end of primary drying, indicating incomplete drying. These foams also experienced collapse, but it was not possible to determine whether this was because the primary drying conditions were too aggressive or because the cycle proceeded to the secondary drying stage before sublimation during primary drying was complete.

Modification 10 used a "quench" whereby the mold was placed into the chamber set at −45° C. in order to cool the solution faster. It is thought that the faster freezing of the quench is freezing the polymer solution before it could form a gel. The drying profile showed intersection of the Pirani and CM curves indicating solvent removal during primary drying. The resulting foams also had a uniform appearance that exhibited mechanical elasticity.

Example 9

Impact of Cooling Rate on Lyophilization

Based off the success of a "quench" thermal treatment in Example 8, the impact of cooling rate as controlled by the quench temperature and method was assessed on the lyophilization of a polymer solution made with a resin that had a fast onset of gelation (Polymer 3 from Example 2).

a) Solution Preparation

Solutions were prepared by weighing out the polymer (Polymer 3 from Example 2) and anhydrous 1,4-dioxane to achieve a 10% (w/w) solution concentration. The two components were combined in an Erlenmeyer flask, which was then fitted with a stir bar and placed in a water bath. The solution was heated at 85° C. with agitation for 1 to 2 hours. After removal from heat, the solution was then filtered through an extra course filter under gentle nitrogen pressure. The filtered solution was then stored covered at room temperature until use.

b) Lyophilization

Prior to lyophilization, the solution was heated to 75° C. for approximately 1 hour. The hot polymer solution was dispensed into a stainless steel mold having 30 cavities; each cavity had a configuration of a strip that was approximately 10 mm×60 mm×3 mm. The lyophilization cycle was then initiated as specified by a computer controlled process steps (recipe). The baseline recipe for this experiment was comprised of the following sequences:

1. Thermal Treatment: The polymer solution was exposed to different cooling rates as defined by the following quench methods:
    Quench #1: The filled mold was placed into the lyophilization unit chamber that was set to a temperature of −10° C. The shelf temperature was then ramped down to −45° C. at a rate of 2° C./min.
    Quench #2: The filled mold was placed into the lyophilization unit chamber that was set to a temperature of −45° C.
    Quench #3: The hot polymer solution was dispensed into a stainless steel mold that had been precooled to −45° C. by storing it at that temperature overnight. After filling the mold, it was placed into the lyophilization unit chamber set to a temperature of −45° C.
    For all quench methods, after quenching and loading the temperature of the unit remained at −45° C. for 1 hr. The temperature was then increased to 3° C. at a rate of 1° C./min and the unit was then held at 3° C. for 1 hour. It was then ramped back to −45° C. at a rate of −0.5° C./min for a hold of 1 hour.
2. Evacuation then commenced by pulling vacuum to 450 mTorr. Once that level was achieved, the unit was held at −45° C. for 2 hours.
3. Primary drying was then started by ramping the unit to −10° C. at a rate of 0.5° C./min and holding for 5 hours. The vacuum level was then decreased to 20 mTorr and the shelf temperature was increased to 10° C. at a rate of 0.25° C./min and held for 3 hrs. The shelf temperature was then increased to 20° C. at a rate of 2° C./min and kept at that level until the cycle was stopped and vacuum was broken with nitrogen.

The lyophilization unit was equipped with a Pirani vacuum gauge, which was used to assess the primary drying via comparative pressure measurement with a capacitance manometer (CM). The primary drying profiles for each quench method are overlayed in FIG. 5. For clarity, only one CM curve was plotted.

The overlay shows that the faster cooling rate, as achieved by dispensing the polymer solution into a prechilled mold, had a faster drying time as indicated by the time where the Pirani and CM curves intersect. The intermediate cooling rate with the quench in the lyophilization unit chamber set to −45° C. also showed intersection of the Pirani and CM curves, but took longer. The slowest cooling rate with the quench of −10° C. did not have intersection Pirani and CM curves within the 5 hour hold for primary drying. The downward trend of the Pirani curve suggests that it may have intersected the CM curve if primary drying was extended.

The foams generated by these quench methods were also tested for residual 1,4-dioxane by gas chromatography. The Quench #1, #2, and #3 foams had residual levels of 3, 1, and 1,306 PPM, respectively.

These results reinforce the thesis that faster cooling rates are needed to freeze the polymer solution before undesirable gel formation in order to enable foam processing by lyophilization.

Example 10

Impact of Polymer Solution Gelation Time on Lyophilization

The block copolymers poly(ε-caprolactone-co-glycolide) of Example 2 were used to study the impact of their onset gelation time on lyophilization.

a) Solution Preparation

Solutions using Polymers 2, 3, 5, 6, and the control from Example 2 were prepared by weighing out the polymer resin and anhydrous 1,4-dioxane to achieve a 10% (w/w) solution concentration. The two components were combined in an Erlenmeyer flask, which was then fitted with a stir bar and placed in a water bath. The solution was heated at 85° C. with agitation for 1 to 2 hours. After removal from heat, the solution was then filtered through an extra course filter under gentle nitrogen pressure. The filtered solution was then stored covered at room temperature until use.

Polymer solutions of 6% (w/w) of Polymers 1 and 3 from Example 2 were prepared in a similar fashion as described above.

b) Lyophilization

Prior to lyophilization, a solution was heated to 75° C. for approximately 1 hour. The hot polymer solution was dispensed into a stainless steel mold having 30 cavities; each cavity had a configuration of a strip that was approximately 10 mm×60 mm×3 mm. The lyophilization cycle was then initiated as specified by a computer controlled process steps (recipe). The baseline recipe for this experiment was comprised of the following sequences:

1. Thermal Treatment: The filled mold was placed into the lyophilization unit chamber that was present to a temperature of −45° C. After 1 hr, the temperature was increased to 3° C. at a rate of 1° C./min and the unit was then held at 3° C. for 1 hour. It was then ramped back to −45° C. at a rate of −0.5° C./min for a hold of 1 hour.
2. Evacuation then commenced by pulling vacuum to 450 mTorr. Once that level was achieved, the unit was held at −45° C. for 2 hours.
3. Primary drying was then started by ramping the unit to −10° C. at a rate of 0.5° C./min and holding for 5 hours. The vacuum level was then decreased to 20 mTorr and the shelf temperature was increased to 10° C. at a rate of 0.25° C./min and held for 3 hours. The shelf temperature was then increased to 20° C. at a rate of 2° C./min and kept at that level until the cycle was stopped and vacuum was broken with nitrogen.

A solution with no polymer (i.e. 100% 1,4-dioxane) was lyophilized in this study to assess the primary drying profile of the solvent alone.

The lyophilization unit was equipped with a Pirani vacuum gauge, which was used to assess the primary drying via comparative pressure measurement with a capacitance manometer (CM). The primary drying profiles for each quench method are overlayed in FIG. 6. For clarity, only one CM curve was plotted.

The overlayed curves show different drying behavior between polymer solutions. The 1,4-dioxane alone shows a very sharp drop from the peak pressure level to crossing the CM level as the solvent is sublimating only in a bulk phase. The polymer solutions have a more gradual slope presumably due to solvent vapor having to navigate a tortuous pore structure and separating from polymer-solvent interactions. The slowest solution the 10% (w/w) solution of Polymer 3, which also showed the fastest onset of gelation as measured in Example 6. The next slowest drying solution was the 6% (w/w) solutions of Polymer 2, which had the second fastest onset of gelation. The slowest gelling solutions (10% (w/w) of the control polymer) showed the fastest drying time. The group of 10% (w/w) solutions of Polymers 2, 5, and 6 that demonstrated intermediate gelling times showed intermediate drying time but surprisingly did not follow the correlation between drying time and onset of gelation times as described above.

There appeared to be a trend of longer drying times associated with polymer solutions that exhibited faster gelation. This would suggest that polymer solutions which exhibited faster gelation required faster cooling rates in order to freeze these solutions faster before undesirable gel formation to enable successful lyophilization into foams.

Example 11

Mechanical Properties of Lyophilized Foams Made from Segmented Block Copolymers from Example 2

The compression properties of foam made with the block copolymer of poly(ε-caprolactone-co-glycolide) produced in Example 2 were evaluated to assess the impact of end blocks and Cap/Gly composition. Foams made from Polymers 2, 3, 5, and 7 were prepared with a constant density, as controlled by a solution concentration of 10% (w/w). In addition, foams made of the random copolymer of poly(ε-caprolactone-co-glycolide) as described in Example 1 were also included as a control.

Foam Preparation a) Solution Preparation

Solutions were prepared by weighing out the polymer resin and anhydrous 1,4-dioxane to achieve a 10% (w/w) solution concentration. The two components were combined in an Erlenmeyer flask, which was then fitted with a stir bar and placed in a water bath. The solution was heated at 85° C. with agitation for 1 to 2 hours. After removal from heat, the solution was then filtered through an extra course filter under gentle nitrogen pressure. The filtered solution was then stored covered at room temperature until use.

b) Lyophilization

Lyophilization of the polymer solutions into a foam construct was carried out in a LyoStar3 unit manufactured by SP Scientific.

Prior to lyophilization, the solution was heated to 75° C. for approximately 1 hour. The hot polymer solution was dispensed into a stainless steel mold having 30 cavities; each cavity had a configuration of a strip that was approximately 10 mm×60 mm×3.5 mm. The lyophilization cycle was then initiated as specified by computer controlled process steps (recipe). The baseline recipe for this experiment was comprised of the following sequences:

1. Thermal Treatment: The filled mold was placed into the lyophilization unit chamber that was present to a temperature of −45° C. After 1 hr, the temperature was increased to 3° C. at a rate of 1° C./min and the unit was then held at 3° C. for 1 hr. It was then ramped back to −45° C. at a rate of −0.5° C./min for a hold of 1 hr.
2. Evacuation then commenced by pulling vacuum to 450 mTorr. Once that level was achieved, the unit was held at −45° C. for 2 hrs.
3. Primary drying was then started by ramping the unit to −10° C. at a rate of 0.5° C./min and held for 5 hrs. The vacuum level was then decreased to 20 mTorr and the shelf temperature was increased to 10° C. at a rate of 0.25° C./min and held for 3 hrs. The shelf temperature was then increased to 20° C. at a rate of 2° C./min and kept at that level until the cycle was stopped and vacuum was broken with nitrogen.

Following lyophilization, the foam strips were removed from the molds and stored under nitrogen until further use.

c) Annealing

Annealing was conducted under nitrogen using a Thermal Product Solutions Blue M Oven. Foams were placed on the shelf of the oven without any fixation. After purging the unit with nitrogen for 1 hour, the temperature of the oven was ramped to 90° C. and held there for 6 hours before returning to room temperature. After annealing, the foam strips were stored under nitrogen until further use.

Compression Testing

The foam strips were all cut to the dimensions of 10 mm×60 mm×3.25 mm. The foams were compressed to different levels and the compressive force was measured using a Mecmesin Mechanical Compression/Tension Load Frame Multi equipped with a 1000N ILC-S Load Cell, 70 mm compression platen, and MultiTest 2.5-xt software. Briefly, foams were compressed to a height of 2.0 mm and the compressive force was recorded after a 15 second hold at that height. The same sample was then sequentially compressed to a height of 1.5 mm, 1.0 mm, and then back to 2.0 mm with the compressive force recorded after 15 seconds at each height. The compressive pressure at each height was calculated by dividing the compressive force by sample area. The recovery ratio was defined as the ratio of the rebound pressure (the second measurement at 2.0 mm after being compressed to 1.0 mm) and the initial pressure at 2 mm. The results of the testing are presented in Table 6.

TABLE 6

Compressive Properties of Foams Made with the Block Copolymer of Poly(ε-caprolactone-co-glycolide)

| Polymer | Center Block Composition (Cap/Gly) | Overall Composition (Cap/Gly) | Compressive Pressure @ 2 mm Height (gf/m m$^2$)* | Rebound Pressure @ 2 mm Height (gf/m m$^2$)* | Recovery Ratio* |
|---|---|---|---|---|---|
| Control | 36/64 | 36/64 | 8.98 ± 0.74 | 4.99 ± 0.43 | 0.56 ± 0.01 |
| 2 | 40/60 | 36/64 | 8.58 ± 0.27 | 4.43 ± 0.14 | 0.52 ± 0.01 |
| 3 | 43/57 | 36/64 | 12.04 ± 1.20 | 5.09 ± 0.64 | 0.42 ± 0.02 |
| 5 | 46/54 | 40/60 | 8.34 ± 0.49 | 4.44 ± 0.30 | 0.53 ± 0.01 |
| 7 | 52/48 | 45/55 | 5.48 ± 0.37 | 2.88 ± 0.24 | 0.52 ± 0.01 |

*Data represents mean ± standard deviation.

Foams made with the control polymer and Polymers 2 and 3 were used to assess the impact of block length at a given overall composition. The smaller block of Polymer 2 did not show an increase in compressive pressure, while the longer block of Polymer 3 showed an increase of approximately 33%. In addition, with an increasing block length there was a reduction in the recovery ratio. However, for the stiffer foam made from Polymer 3 this still resulted in a higher rebound pressure than the control polymer.

Foams made with Polymers 3, 5, and 7 all had the same block length but different compositions with the caprolactone increasing from 36 to 40 to 45, respectively. The compression is shown to decrease with the increasing caprolactone content. In contrast, the recovery ratio increased with increasing caprolactone content in the random segment.

Example 12

In Vitro Degradation Behavior of Lyophilized Foams made from Segmented Block Copolymers of Example 2

The in vitro degradation behavior of foam made with the block copolymers of poly(ε-caprolactone-co-glycolide) produced in Example 2 was evaluated to assess the impact of end blocks and Cap/Gly composition. This was assessed by measuring the compression force of the foam compressed to a fixed height while undergoing hydrolysis. Foams made with Polymers 2, 3, 5 and 6 as well as the random copolymer of Example 1 were prepared as described in Example 11.

In Vitro Degradation Under Continuous Compression

Foams were tested under continuous compression to simulate an application where a foam would serve as a cushion or defect filler. The foam strips were all cut to the dimensions of 10 mm×60 mm×3.25 mm. The foams were then placed into a fixture that utilized a platen to compress the foam to a height of 2.0 mm. Above the platen was a load cell that continuously recorded the compressive force using a Honeywell SC3004 Data Acquisition Unit at a rate of 5 Hz. The entire fixture, including the foam sample, was then submerged into a bath of phosphate buffer saline at a pH of 7.27 that was maintained at a temperature of 37° C. The compressive force was recorded for a period of 28 days when the experiment was stopped. The plots of compressive force over time were then used to determine the degradation coefficient expressed as the decay coefficient of the exponential fit of the curve. The compressive forces at day 1 and day 28, as well as the degradation coefficient are shown in Table 7.

TABLE 7

Compression of Foams Made with the Block Copolymer of Poly(ε-caprolactone-co-glycolide) Undergoing Hydrolytic Degradation Under a Continuous Compressive Load.

| Polymer | Center Block Composition (Cap/Gly) | Overall Composition Cap/Gly | Compressive Pressure @ 2 mm Height on Day 1 (gf/mm$^2$) | Compressive Pressure @ 2 mm Height on Day 28 (gf/mm$^2$) | Degradation Coefficient |
|---|---|---|---|---|---|
| Control | 36/64 | 36/64 | 5.77 | 0.37 | 0.099 |
| 2 | 40/60 | 36/64 | 6.55 | 0.75 | 0.068 |
| 3 | 43/57 | 36/64 | 8.32 | 1.05 | 0.065 |
| 5 | 46/54 | 40/60 | 5.97 | 0.66 | 0.063 |
| 6 | 49/51 | 40/60 | 6.54 | 0.73 | 0.065 |

The results show a decrease in the degradation coefficient for the copolymers with end blocks, indicating a longer degradation profile. Comparing the control polymer and Polymers 2 and 3 on the one hand and Polymers 5 and 6 on the other hand, showed that the compressive strength at both day 1 and day 28 increases with increasing end block. In addition, comparing Polymers 3 and 5 showed that increasing the caprolactone content in the random segment reduced the strength retained at both day 1 and day 28.

It was also observed that the integrity of foams as they were degrading was different between those made with polymers with increasing caprolactone content. Foams made with Polymers 5 and 6 had remained as one continuous piece of foam throughout the test period of 28 days. Those made with Polymers 2 and 3 (with lower caprolactone content) were found to fracture into several segments.

Example 13

Effect of Annealing

The level of crystallinity and crystal size of the lyophilized foams of the present invention depend on the polymer architecture, but can be adjusted by exposing the foams to dry heat at a selected temperature for a sufficiently effective period of time. In turn, this allows for fine tuning of the dimensional stability and mechanical properties of the foams. Foams were annealed at temperatures ranging from 60° C. to 120° C. with durations ranging from 1-12 hours. In general, the higher the annealing temperature, the more shrinkage was observed. Interestingly, shrinking did occur within the first hour of annealing after which no further shrinkage was observed.

Table 8 shows dimensional changes for foams based on the prior art control polymer and Polymer 3 of the present invention. As can be seen, the dimensional stability of the end block containing polymers is significantly higher than the material prepared that was analogous to Vyakarnam et al. The change in dimensions appears to be roughly equivalent for all three dimensions.

TABLE 8

Change in Volume as Expressed as Percent Shrinkage in Annealed Foams Made with the Block Copolymer of Poly(ε-caprolactone-co-glycolide).

| | Percent Shrinkage at Annealing Condition* | | |
|---|---|---|---|
| Polymer | 70° C., 6 hrs | 90° C., 6 hrs | 110° C., 6 hrs |
| Control | 5.36 ± 0.17 | 10.66 ± 0.77 | 55.87 ± 3.02 |
| 3 | 3.51 ± 0.35 | 7.24 ± 0.73 | 9.93 ± 0.96 |

*Data represents mean ± standard deviation

FIG. 7 shows the impact of different annealing conditions on the thermal behavior of foams based on Polymer 5. At low temperature there is a broad distribution of crystallite sizes, which is reflected by a broad melt transition with multiple peaks. The higher the annealing temperature, the narrower this distribution becomes until a narrow distribution around 120° C. is achieved by annealing at 110° C. A small level of smaller crystals can be re-introduced by a secondary annealing step at a lower temperature. Interestingly, there was no significant difference observed for the overall level of crystallinity.

Shrinkage occurred in every dimension but was most significant in thickness. As can be seen in Table 9, shrinkage was relatively minor at lower temperatures but became more significant at 110° C. In general, the higher the annealing temperature, the more shrinkage was observed. Interestingly, shrinking did occur within the first hour of annealing after which no further shrinkage was observed.

TABLE 9

Percent Shrinkage in Thickness for Annealed Foams Made with Polymer 5 of Example 2.

| Annealing Condition | Percent Shrinkage in Thickness (%)* |
|---|---|
| 60° C., 4 hrs | 1.70 ± 1.23 |
| 60° C., 4 hrs + 110° C., 4 hrs | 7.93 ± 1.01 |
| 85° C., 4 hrs | 2.66 ± 1.63 |
| 85° C., 4 hrs + 60° C., 4 hrs | 2.62 ± 0.47 |
| 90° C., 4 hrs | 3.32 ± 0.93 |
| 110° C., 4 hrs | 7.82 ± 1.45 |
| 110° C., 4 hrs + 60° C., 4 hrs | 7.40 ± 1.40 |
| 110° C., 4 hrs + 85° C., 4 hrs | 6.86 ± 0.92 |
| 120° C., 6 hrs | 12.92 ± 2.83 |

*Data represents mean ± standard deviation

The impact of the annealing conditions on the mechanical performance of foams based on Polymer 5 is shown in Table 10. The foams were compressed in a step-wise approach as described in Example 11. Surprisingly, the annealing conditions had little effect on the compressive force value for the foams but had a significant effect on the recovery ratio which is a proxy for the rebound of the foams. In general, the higher the annealing temperature, the higher was the observed rebound. However the extent to which one can increase temperature is limited by shrinkage since annealing at 120° C. results in an unacceptable shrinkage of 12.92%.

TABLE 10

Compressive Properties of Annealed Foams Made from Polymer 5 of Example 2.

| Annealing Treatment | Compressive Pressure @ 2 mm Height (gf/mm$^2$)* | Rebound Pressure @ 2.0 mm Height (gf/mm$^2$)* | Recovery Ratio* |
|---|---|---|---|
| 60° C., 4 hrs | 8.40 ± 1.01 | 3.49 ± 0.36 | 0.42 ± 0.01 |
| 80° C., 4 hrs | 8.23 ± 0.99 | 4.11 ± 0.51 | 0.50 ± 0.01 |
| 110° C., 4 hrs | 7.69 ± 1.01 | 4.28 ± 0.53 | 0.56 ± 0.01 |
| 110° C., 4 hrs + 60° C., 4 hrs | 8.30 ± 0.63 | 4.69 ± 0.36 | 0.57 ± 0.01 |
| 110° C., 4 hrs + 85° C., 4 hrs | 7.65 ± 1.35 | 4.30 ± 0.75 | 0.56 ± 0.01 |

*Data represents mean ± standard deviation

Foams prepared from Polymer 5 annealed at various temperatures were evaluated for compression over time in the in vitro degradation method as described in Example 12. As can be seen in Table 11, initially there was not much difference observed between the various annealing conditions, but at the later time point, the samples that were annealed at the highest temperature (110° C.) retained significantly less strength than those annealed at lower temperatures.

TABLE 11

Compression of Annealed Foams Made with Polymer 5 of Example 2 Undergoing Hydrolytic degradation Under a Continuous Compressive Load.

| Annealing Condition | Compressive Pressure @ 2 mm Height on Day 1 (gf/mm$^2$) | Compressive Pressure @ 2 mm Height on Day 28 (gf/mm$^2$) | Degradation Coefficient gf/(mm$^2$ · day) |
|---|---|---|---|
| 60° C., 4 hrs | 5.25 | 0.78 | 0.069 |
| 90° C., 4 hrs | 4.99 | 0.77 | 0.069 |
| 110° C., 4 hrs | 5.44 | 0.51 | 0.086 |
| 110° C., 4 hrs + 60° C., hrs | 5.02 | 0.52 | 0.080 |

Although this invention has been shown and described with respect to detailed embodiments thereof, it will be understood by those skilled in the art that various changes in form and detail thereof may be made without departing from the spirit and scope of the claimed invention.

We claim:

1. A method of making an absorbable foam by a lyophilization process, comprising the steps of:
   a) providing an absorbable polymer comprising a semicrystalline, absorbable, segmented block copolymer having a random center block segment of repeating units of polymerized glycolide and polymerized epsilon-caprolactone, and an end block segment that comprises predominantly polymerized glycolide, wherein the mole ratio of polymerized glycolide to polymerized epsilon-caprolactone of the entire segmented copolymer is about 55:45 to about 65:35, and having a mole ratio of polymerized glycolide to polymerized epsilon-caprolactone in the random center block segment between about 45:55 to about 52:48;
   b) dissolving a sufficient quantity of the copolymer in a suitable solvent to form a lyophilizing solution;
   c) pouring at least a part of the solution at a sufficiently effective temperature to prevent premature gel formation into a suitable mold;
   d) freezing the solution at a fast enough rate to prevent premature gel formation in order to facilitate solvent removal in a subsequent lyophilization process; and,
   e) subjecting the frozen solution in the mold to a lyophilizing process, wherein the pressure is lowered and heat is applied to sublimate the solvent and form an absorbable foam.

2. The method of claim 1, wherein the copolymer has an inherent viscosity between about 0.5 dL/g and about 2.5 dl/g, as measured in a 0.1 g/dl solution of HFIP at 25° C.

3. The method of claim 1, wherein the solvent is selected from the group consisting of 1,4-dioxane, a mixture of at least 90 weight percent 1,4-dioxane and no more than 10 weight percent water, and a mixture of at least 90 weight percent 1,4-dioxane and no more than 10 weight percent of an organic alcohol having a molecular weight of less than 1,500.

4. The method of claim 1 wherein the solid content of the lyophilizing solution is between about 3 and about 20 weight percent.

5. The method of claim 1 wherein the weight percentage of the dissolved copolymer in the lyophilizing solution formed by step b) is between about 5 and about 15 weight percent.

6. The method of claim 1 wherein the lyophilizing solution is poured at a temperature above 50° C. into the suitable mold.

7. The method of claim 1, wherein the rate of freezing is equal to or faster than −5° C. per minute.

8. The method of claim 1 wherein the rate of freezing is equal to or faster than −10° C. per minute.

9. The method of claim 1, wherein the absorbable polymer foam has a Degradation Coefficient at 2 mm height after 28 days of incubation in a buffer of pH 7.27 at 37° C. under continuous compression not greater than 0.065, wherein the degradation coefficient is determined from plots of compressive force over time, with the coefficient expressed as the decay coefficient of the exponential fit of the curve.

* * * * *